US010653488B2

(12) United States Patent
Kang et al.

(10) Patent No.: US 10,653,488 B2
(45) Date of Patent: *May 19, 2020

(54) SYSTEM AND METHOD FOR ROBOTIC SURGERY

(71) Applicant: MAKO Surgical Corp., Fort Lauderdale, FL (US)

(72) Inventors: Hyosig Kang, Weston, FL (US); Scott Nortman, Sunrise, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 223 days.

This patent is subject to a terminal disclaimer.

(21) Appl. No.: 15/958,945

(22) Filed: Apr. 20, 2018

(65) Prior Publication Data

US 2018/0235718 A1   Aug. 23, 2018

Related U.S. Application Data

(60) Continuation of application No. 14/736,792, filed on Jun. 11, 2015, now Pat. No. 9,974,613, which is a (Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 17/16* (2013.01); *A61B 17/1622* (2013.01); *A61B 34/20* (2016.02); *A61B 34/37* (2016.02); *A61B 34/75* (2016.02); *A61B 34/76* (2016.02); *A61B 90/03* (2016.02); *A61B 2017/00477* (2013.01)

(58) Field of Classification Search
CPC ......... A61B 34/30; A61B 34/76; A61B 34/75; A61B 34/00; A61B 17/16; A61B 17/1622
See application file for complete search history.

(56) References Cited

U.S. PATENT DOCUMENTS 8,010,180 B2   8/2011   Quaid et al.
9,010,002 B2   4/2015   Popa-Simil
(Continued)

OTHER PUBLICATIONS

Jan Vascak, "Navigation of Mobile Robots Using Potential Fields and Computational Intelligence Means", Acta Polytechnica Hungarica, 2007, p. 63-74, vol. 4, No. 1.

*Primary Examiner* — Christopher J Beccia
(74) *Attorney, Agent, or Firm* — Foley & Lardner LLP

(57) ABSTRACT

A robotic surgery method for cutting a bone of a patient includes characterizing the geometry and positioning of the bone and manually moving a handheld manipulator, the handheld manipulator operatively coupled to a bone cutting tool having an end effector portion, to cut a portion of the bone with the end effector portion. The handheld manipulator further comprises a manipulator housing and an actuator assembly movably coupled between the manipulator housing and the bone cutting tool. The method further includes causing the actuator assembly to automatically move relative to the manipulator housing to maintain the end effector portion of the tool within a desired bone cutting envelope in response to movement of the manipulator housing relative to the bone.

20 Claims, 26 Drawing Sheets

Related U.S. Application Data division of application No. 13/276,099, filed on Oct. 18, 2011, now Pat. No. 9,060,794.

(51) Int. Cl.
*A61B 34/20* (2016.01)
*A61B 17/16* (2006.01)
*A61B 34/37* (2016.01)
*A61B 90/00* (2016.01)
*A61B 17/00* (2006.01)

(56) References Cited

U.S. PATENT DOCUMENTS

| | | | |
|---|---|---|---|
| 9,060,794 B2* | 6/2015 | Kang | A61B 17/1622 |
| 9,814,468 B2* | 11/2017 | Kang | A61B 17/1622 |
| 9,974,613 B2* | 5/2018 | Kang | A61B 17/1622 |
| 2005/0171553 A1 | 8/2005 | Schwarz et al. | |
| 2008/0070752 A1 | 3/2008 | Einav | |
| 2009/0012532 A1* | 1/2009 | Quaid | A61B 90/361 |
| | | | 606/130 |
| 2010/0094312 A1 | 4/2010 | Ruiz Morales et al. | |
| 2012/0143084 A1* | 6/2012 | Shoham | A61B 17/1675 |
| | | | 600/567 |
| 2013/0060278 A1 | 3/2013 | Bozung et al. | |
| 2015/0182285 A1 | 7/2015 | Yen et al. | |
| 2015/0305761 A1 | 10/2015 | Kang et al. | |

* cited by examiner

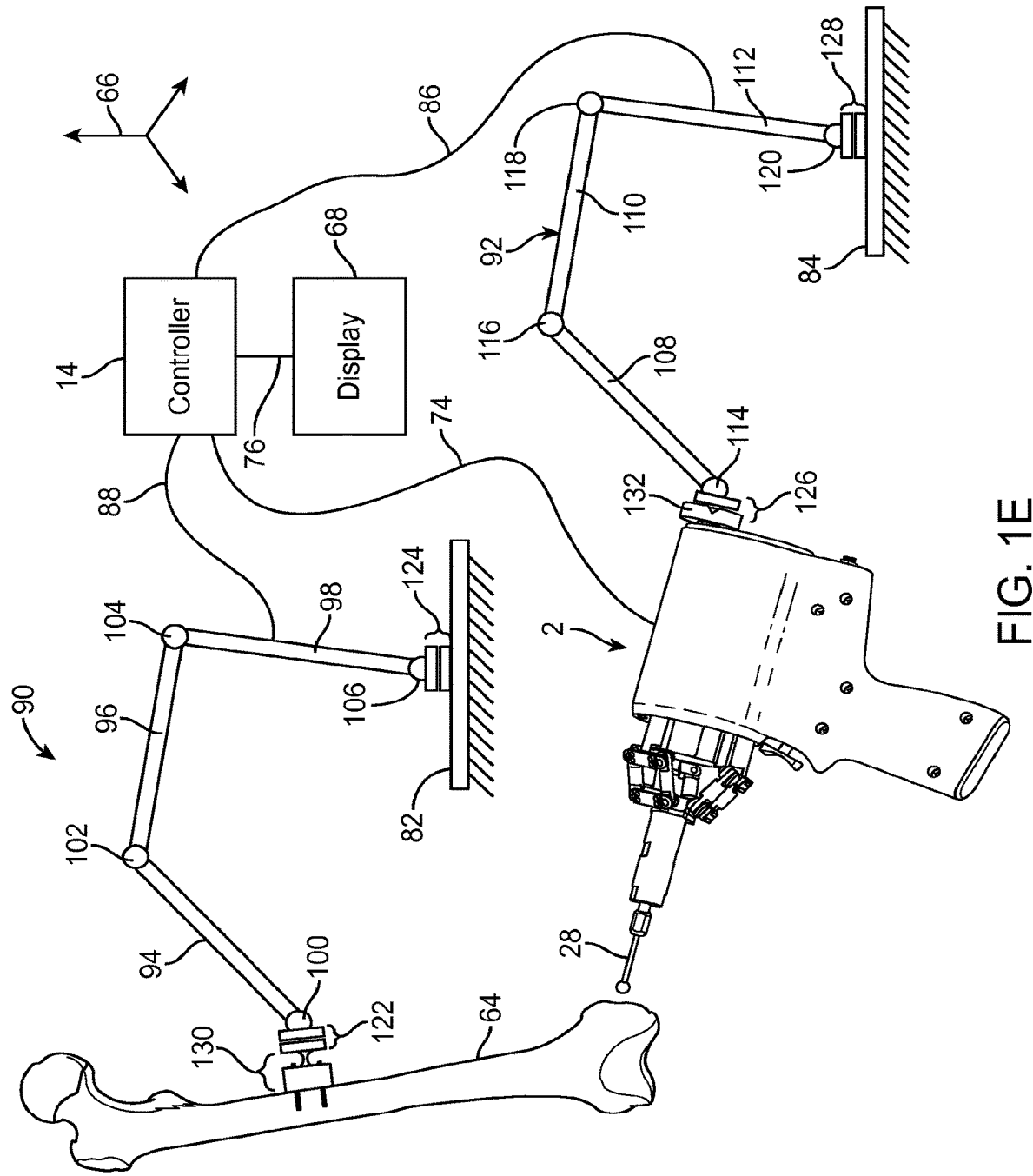

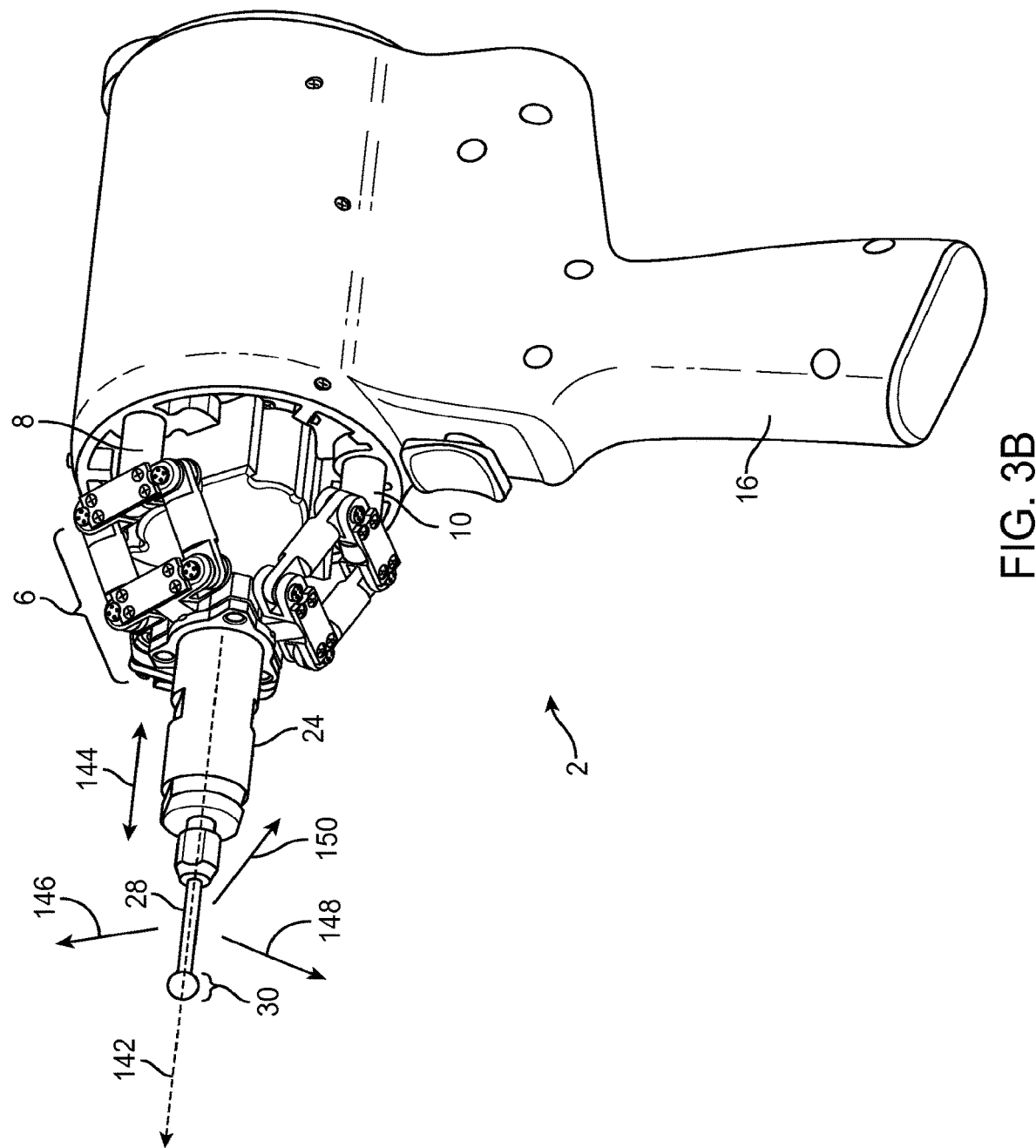

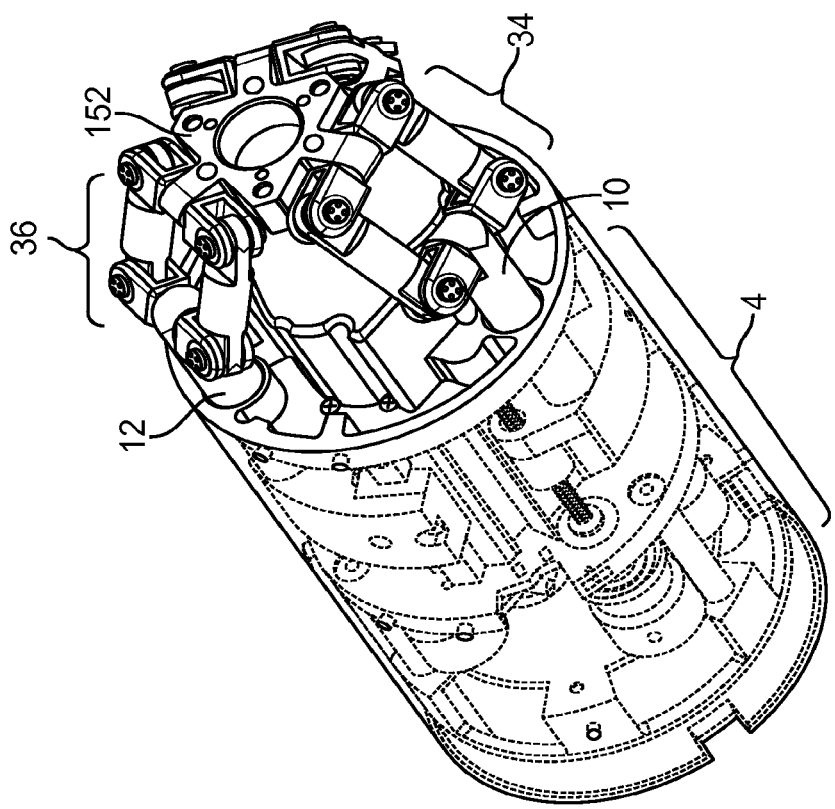
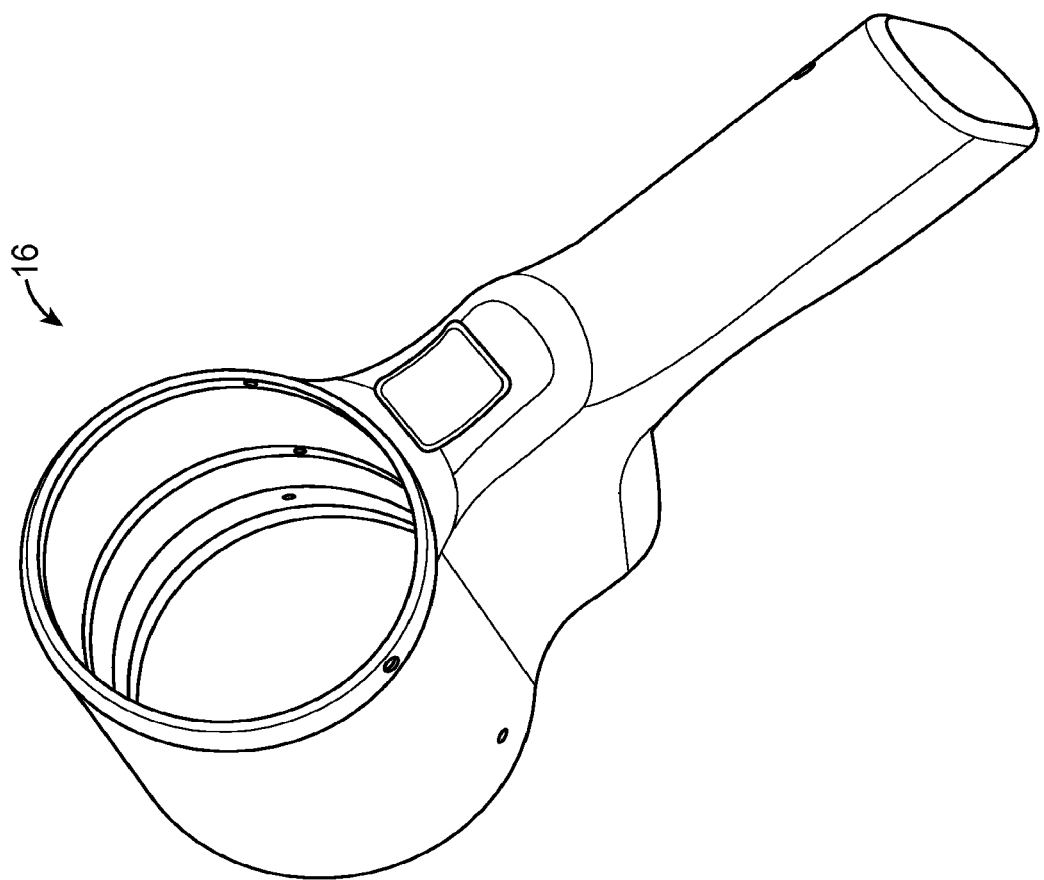
FIG. 3E
FIG. 3D

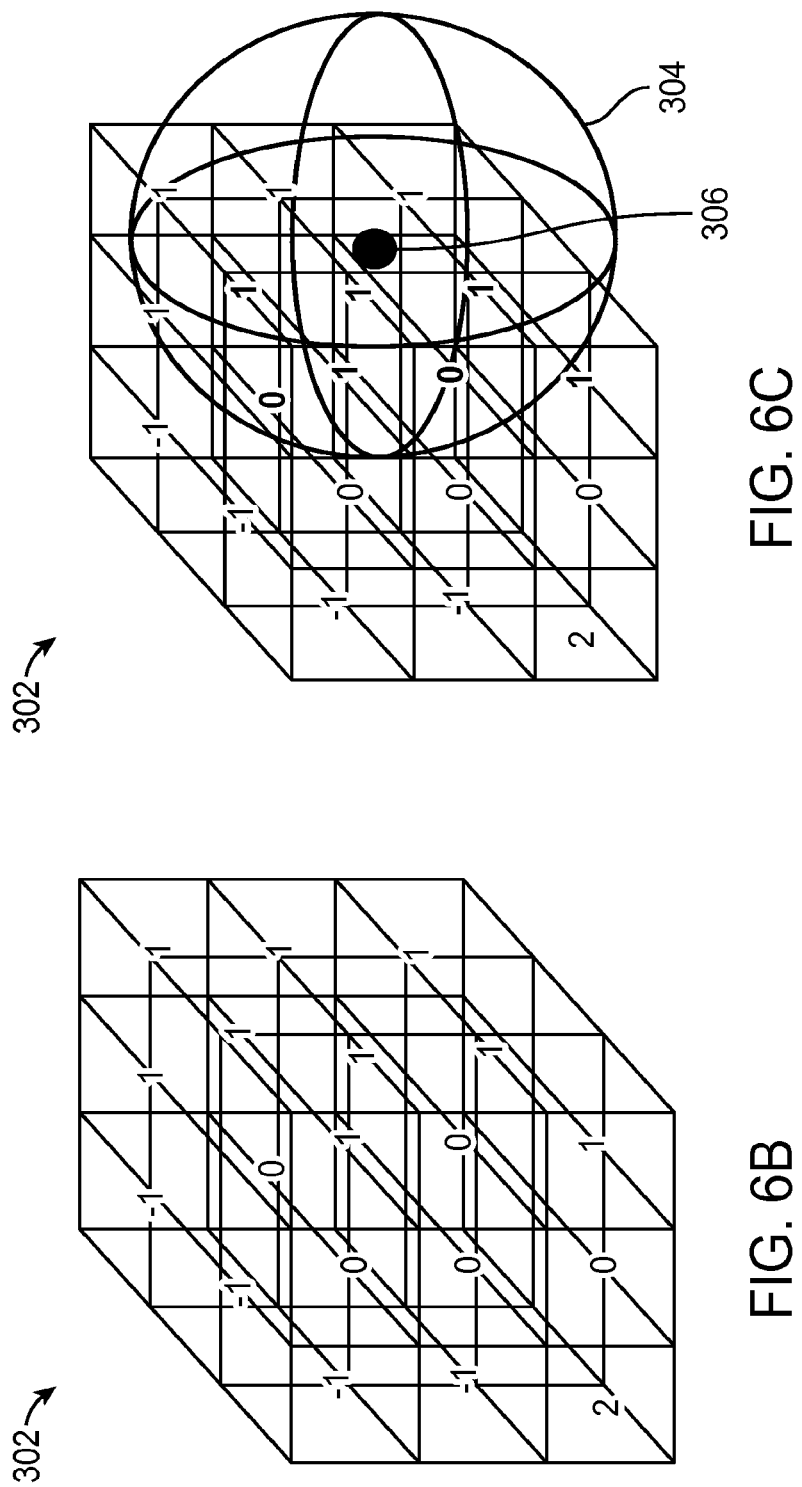

SYSTEM AND METHOD FOR ROBOTIC SURGERY

CROSS-REFERENCE TO RELATED APPLICATIONS

This application is a continuation of U.S. application Ser. No. 14/736,792, filed Jun. 11, 2015, which is a divisional of U.S. application Ser. No. 13/276,099, filed Oct. 18, 2011, both of which are hereby incorporated by reference herein in their entireties.

FIELD OF THE INVENTION

The present invention relates generally to surgical systems, and more specifically to systems and methods for positioning and orienting tools during surgical procedures.

BACKGROUND

Minimally invasive surgery (MIS) is the performance of surgery through incisions that are considerably smaller than incisions used in traditional surgical approaches. For example, in an orthopedic application such as total knee replacement surgery, an MIS incision length may be in a range of about 4 to 6 inches, whereas an incision length in traditional total knee surgery is typically in a range of about 6 to 12 inches. As a result of the smaller incision length, MIS procedures are generally less invasive than traditional surgical approaches, which minimizes trauma to soft tissue, reduces post-operative pain, promotes earlier mobilization, shortens hospital stays, and speeds rehabilitation.

MIS presents several challenges for a surgeon. For example, in minimally invasive orthopedic joint replacement, the small incision size may reduce the surgeon's ability to view and access the anatomy, which may increase the complexity of sculpting bone and assessing proper implant position. As a result, accurate placement of implants may be difficult. Conventional techniques for counteracting these problems include, for example, surgical navigation, positioning the subject patient limb for optimal joint exposure, and employing specially designed, downsized instrumentation and complex surgical techniques. Such techniques, however, typically require a large amount of specialized instrumentation, a lengthy training process, and a high degree of skill. Moreover, operative results for a single surgeon and among various surgeons are not sufficiently predictable, repeatable, and/or accurate. As a result, implant performance and longevity varies among patients.

To assist with MIS and conventional surgical techniques, advancements have been made in surgical instrumentation, and in technologies for understanding the spatial and rotational relationships between surgical instruments and tissue structures with which they are intervening during surgery. For example, instruments for calcified tissue intervention that are smaller, lighter, and more maneuverable than conventional instruments have become available, such as handheld instruments configured to be substantially or wholly supported manually as an operator creates one or more holes, contours, etc. in a subject bony tissue structure. In certain surgical scenarios, it is desirable to be able to use such handheld type instrumentation while understanding where the working end of the pertinent tools are relative to the anatomy. In particular, it is desirable to be able to control the intervention such that there are no aberrant aspects, wherein bone or other tissue is removed outside of the surgical plan, as in a situation wherein a surgical operator has a hand tremor that mistakenly takes the cutting instrument off path, or wherein a patient moves unexpectedly, thereby taking the instrument off path relative to subject tissue structure. There is a need for handheld systems that are capable of assisting a surgeon or other operator intraoperatively by compensating for aberrant movements or changes pertinent to the spatial relationship between associated instruments and tissue structures.

BRIEF DESCRIPTION OF THE DRAWINGS

FIG. 1E illustrates an embodiment wherein two mechanical tracker linkages are utilized to monitor the spatial positions of a targeted tissue structure and an interventional tool.

FIGS. 3A-3M illustrate aspects of a handheld tissue cutting tool featuring a motion compensation mechanism.

FIGS. 6A-6C illustrate aspects of embodiments wherein potential fields may be utilized to further control motion of the interventional tool.

SUMMARY

Figure 1A:
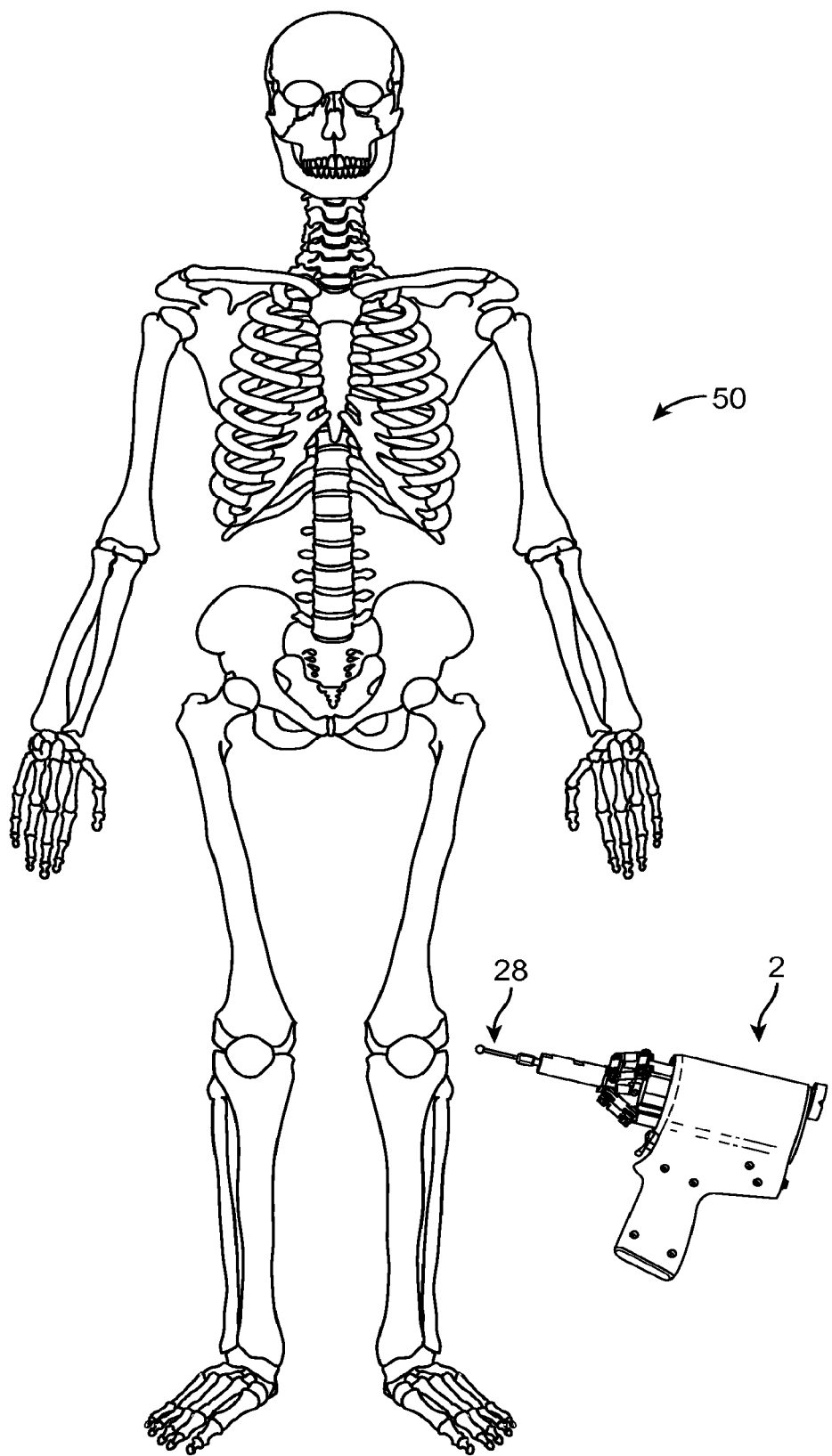
FIG. 1A illustrates a handheld bone cutting tool adjacent various tissue structures of the skeleton.

One embodiment is directed to a robotic surgery system for cutting a bone of a patient, comprising: a handheld manipulator configured to be manually moved in a global coordinate system relative to the bone, the handheld manipulator comprising: a bone cutting tool comprising an end effector portion, a frame assembly, and a motion compensation assembly movably coupled to the frame assembly and bone cutting tool; and a controller operatively coupled to the manipulator and configured to operate one or more actuators within the frame assembly to cause the motion compensation assembly to automatically move relative to the frame assembly to defeat aberrant movement of the bone cutting tool that would place the end effector portion of the tool out of a desired bone cutting envelope that is based at least in part upon one or more images of the bone, while allowing the bone cutting tool to continue cutting one or more portions of the bone. The end effector portion may comprise a burr. The system further may comprise a housing coupled to the frame assembly. The housing may comprise a handle configured to be manually grasped by a human hand. The housing may be operatively coupled to a gravity compensation mechanism. The frame assembly may comprise one or more motors operatively coupled to one or more structural members, the one or more structural members being coupled to the motion compensation assembly. The one or more structural members may be configured to insert and retract relative to the frame assembly, causing an associated movement of the motion compensation assembly. The one or more motors may be operatively coupled to the one or more structural members via one or more lead screw assemblies configured to insert and retract each of the structural members in accordance with rotation of the one or more motors. The system may further comprise one or more belts operatively coupled between each of the one or more motors and one or more lead screw assemblies, the one or more belts configured to transfer rotational motion from the one or more motors to the one or more lead screw assemblies. The system may further comprise one or more gears intercoupled between at least one of the one or more lead screw assemblies and one or more motors, the gears configured to transfer rotational motion from the one or more motors to the one or more lead screw assemblies. The system may further comprise a tool drive assembly intercoupled between the bone cutting tool and the motion compensation assembly. The tool drive assembly may comprise a motor configured to actuate the bone cutting tool. The motor may be configured to controllably move the bone cutting tool. The motor may be operatively coupled to the controller such that the controller may control or stop a cutting velocity of the bone cutting tool. The controller may be configured to change the cutting velocity of the bone cutting tool based at least in part upon a signal from a sensor indicating that the end effector portion is being moved toward a boundary of the desired bone cutting envelope. The controller may be configured to modulate the cutting velocity of the bone cutting tool based at least in part upon the location of the tool within the desired bone cutting envelope. The controller may be configured to generally reduce the cutting velocity of the bone cutting tool when the tool is moved adjacent an edge of the desired bone cutting envelope. The controller may be configured to modulate the cutting velocity of the bone cutting tool based at least in part upon the location of the tool within a predetermined workspace of the handheld manipulator. The controller may be configured to generally reduce the cutting velocity of the bone cutting tool when the tool is moved adjacent the edge of the predetermined workspace. The system may further comprise a tracking subsystem configured to determine a position of the end effector portion of the bone cutting tool relative to the global coordinate system. The system may further comprise a tracking subsystem configured to determine a position of one or more portions of the desired bone cutting envelope relative to the global coordinate system. The system may further comprise a tracking subsystem configured to determine a position of the end effector portion of the bone cutting tool relative to one or more portions of the desired bone cutting envelope. The tracking subsystem may comprise a tracking element selected from the group consisting of: a mechanical tracker linkage, an optical tracker, an ultrasonic tracker, and an ultra-wide-band tracker. The tracking system may comprise a mechanical tracker linkage having at least two substantially rigid portions coupled by at least one movable joint. The tracking system may comprise a mechanical tracker linkage having at least three substantially rigid portions coupled in a series configuration by two or more movable joints. The series configuration may comprise a proximal end and a distal end, each of which is coupled to a kinematic quick-connect fitting. A proximal kinematic quick-connect fitting may be configured to be fixedly and removably coupled to the bone. A distal kinematic quick-connect fitting may be configured to be fixedly and removably coupled to the frame assembly. The controller may be configured to defeat aberrant movement of the bone cutting tool that is associated with relatively high frequency unintended motion. The relatively high frequency unintended motion may have a frequency between about 1 Hz and about 12 Hz. The controller may be configured to defeat aberrant movement of the bone cutting tool that is associated with relatively low frequency unintended motion. The relatively low frequency unintended motion may have a frequency between about 0 Hz and about 1 Hz. The controller may be configured to defeat aberrant movement of the bone cutting tool that is associated with both relatively low frequency unintended motion and relatively high frequency unintended motion. The unintended motion may have a frequency between about 0 Hz and about 12 Hz. The one or more images may be acquired using an imaging modality selected from the group consisting of: computed tomography, radiography, ultrasound, and magnetic resonance. The controller may be configured to modulate the tool path automatically based at least in part upon potential field analysis. The controller may be configured to execute modulation of the tool path through motion compensation. The controller may be configured to execute modulation of the tool path through haptic resistance to motion of the handheld manipulator.

Another embodiment is directed to a robotic surgery method for cutting a bone of a patient, comprising: acquiring image information regarding the bone; manually moving a handheld manipulator, the handheld manipulator operatively coupled to a bone cutting tool having an end effector portion, to cut a portion of the bone with the end effector portion; and automatically compensating for aberrant movement of the bone cutting tool that would place the end effector portion of the tool out of a desired bone cutting envelope that is based at least in part upon the image information, while allowing the bone cutting tool to continue cutting one or more portions of the bone. The handheld manipulator may be configured to be manually moved in a global coordinate system relative to the bone. The end effector portion may be configured to be moved at a preferred bone cutting velocity. The method may further comprise modulating the cutting velocity based at least in part upon the location of the end effector portion within a desired bone cutting envelope. The method may further comprise generally reducing the cutting velocity of the end effector portion when the end effector portion is moved adjacent an edge of a desired bone cutting envelope. The method may further comprise modulating the cutting velocity of the end effector portion based at least in part upon the location of the end effector portion within a predetermined workspace of the handheld manipulator. The method may further comprise generally reducing the cutting velocity of the end effector portion when the end effector portion is moved adjacent an edge of the predetermined workspace of the handheld manipulator. The end effector portion may be allowed to continue cutting one or more portions of the bone at the preferred cutting angular velocity while automatically compensating for aberrant movement of the bone cutting tool. Automatically compensating for aberrant movement of the bone cutting tool may comprise controllably moving the cutting tool relative to the handheld manipulator. Controllably moving may comprise axially moving the cutting tool in a direction substantially coaxial with a longitudinal axis of a previous position of the cutting tool. Controllably moving may comprise adjusting a pitch or yaw of the cutting tool relative to a longitudinal axis of a previous position of the cutting tool. Controllably moving may comprise moving the cutting tool in two or more degrees of freedom. Acquiring image information may comprise using an imaging modality selected from the group consisting of: computed tomography, radiography, ultrasound, and magnetic resonance. The method further may comprise creating a preoperative surgical plan based at least in part upon the image information, and utilizing the preoperative surgical plan to create the desired bone cutting envelope. Controllably moving the cutting tool relative to the handheld manipulator may comprise operating a motor. Operating the motor may operate a lead screw mechanism operatively coupled to the motor. The method may further comprise determining that an attempted movement is an aberrant movement. Determining that an attempted movement is an aberrant movement may comprise tracking the spatial positioning of the bone and the end effector portion of the cutting tool. Tracking the spatial positioning of the bone may comprise monitoring the positions of one or more optical tracking markers that are coupled to the bone. Tracking the spatial positioning of the bone may comprise monitoring the positions of one or more joints of a mechanical tracker linkage that is coupled to the bone. Tracking the spatial positioning of the end effector portion of the cutting tool may comprise monitoring the positions of one or more optical tracking markers that are coupled to the cutting tool. Tracking the spatial positioning of the end effector portion of the cutting tool may comprise monitoring the positions of one or more joints of a mechanical tracker linkage that is coupled to the cutting tool. The method may further comprise intercoupling a mechanical tracker linkage between the bone and the handheld manipulator to facilitate monitoring of the three dimensional relative spatial relationship between the bone and the handheld manipulator. Intercoupling may comprise removably coupling at least one end of the mechanical tracker with a kinematic quick-connect fitting. The method may further comprise modulating the tool path automatically based at least in part upon potential field analysis or alternate heuristic algorithm, such as a spatial state machine heuristic. Modulating the tool path may comprise executing motion compensation based upon the potential field analysis or alternate heuristic algorithm. Modulating the tool path may comprise haptically resisting motion of the handheld manipulator.

Another embodiment is directed to a robotic surgery method for cutting a bone of a patient, comprising: characterizing the geometry and positioning of the bone; manually moving a handheld manipulator, the handheld manipulator operatively coupled to a bone cutting tool having an end effector portion, to cut a portion of the bone with the end effector portion; and automatically compensating for aberrant movement of the bone cutting tool that would place the end effector portion of the tool out of a desired bone cutting envelope that is based at least in part upon the image information, while allowing the bone cutting tool to continue cutting one or more portions of the bone. Characterizing the geometry and position of the bone may comprise analyzing image information acquired from the bone. The method may further comprise acquiring the image information using a modality selected from the group consisting of: computed tomography, radiography, ultrasound, and magnetic resonance.

DETAILED DESCRIPTION

Figure 1B:
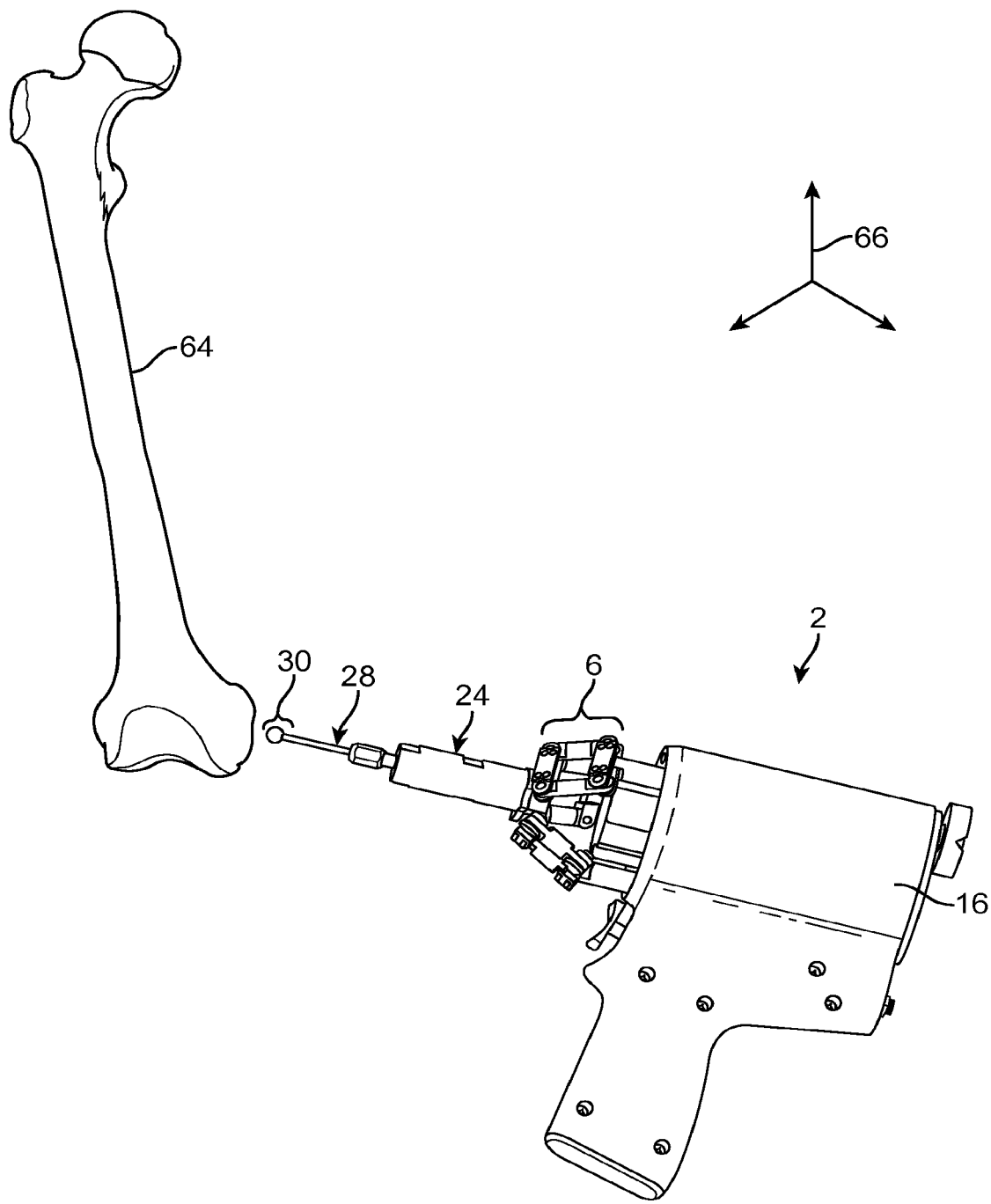
FIG. 1B illustrates a close in view of a handheld bone cutting tool adjacent a femur, both of which reside in a common global coordinate system.

Referring to FIG. 1A, as discussed briefly above, it may be useful in certain surgical scenarios to utilize a handheld manipulator (2) coupled to a tool (28) such as a bone removal tool, in interventions involving various aspects of the human skeleton (50). For example, as shown more closely in FIG. 1B, it may be useful to use a handheld manipulator (2) and associated tool (28) with an end effector distal portion (30) such as a bone burring or osteotomy tip to remove portions of a femur (64) of a patient in a joint resurfacing operation, such as those involving prostheses available from MAKO Surgical Corporation of Fort Lauderdale, Fla. The illustrative configuration comprises the handheld manipulator (2) with a motion compensation assembly (6) that couples the tool (28) and an associated tool driver (24) to the main manipulator housing (16).

In embodiments wherein activity of the motion compensation assembly (6) is to be utilized to assist in preventing aberrant bone removal tool pathways that stray from a predetermined bone removal plan or "envelope", it is desirable to understand where both the subject tissue structure (here the femur 64) and the tool (28) are relative to some common coordinate system, such as a global coordinate system (66) of the operating room. Such an understanding may be developed using various position sensing or tracking technologies.

Figure 1C:
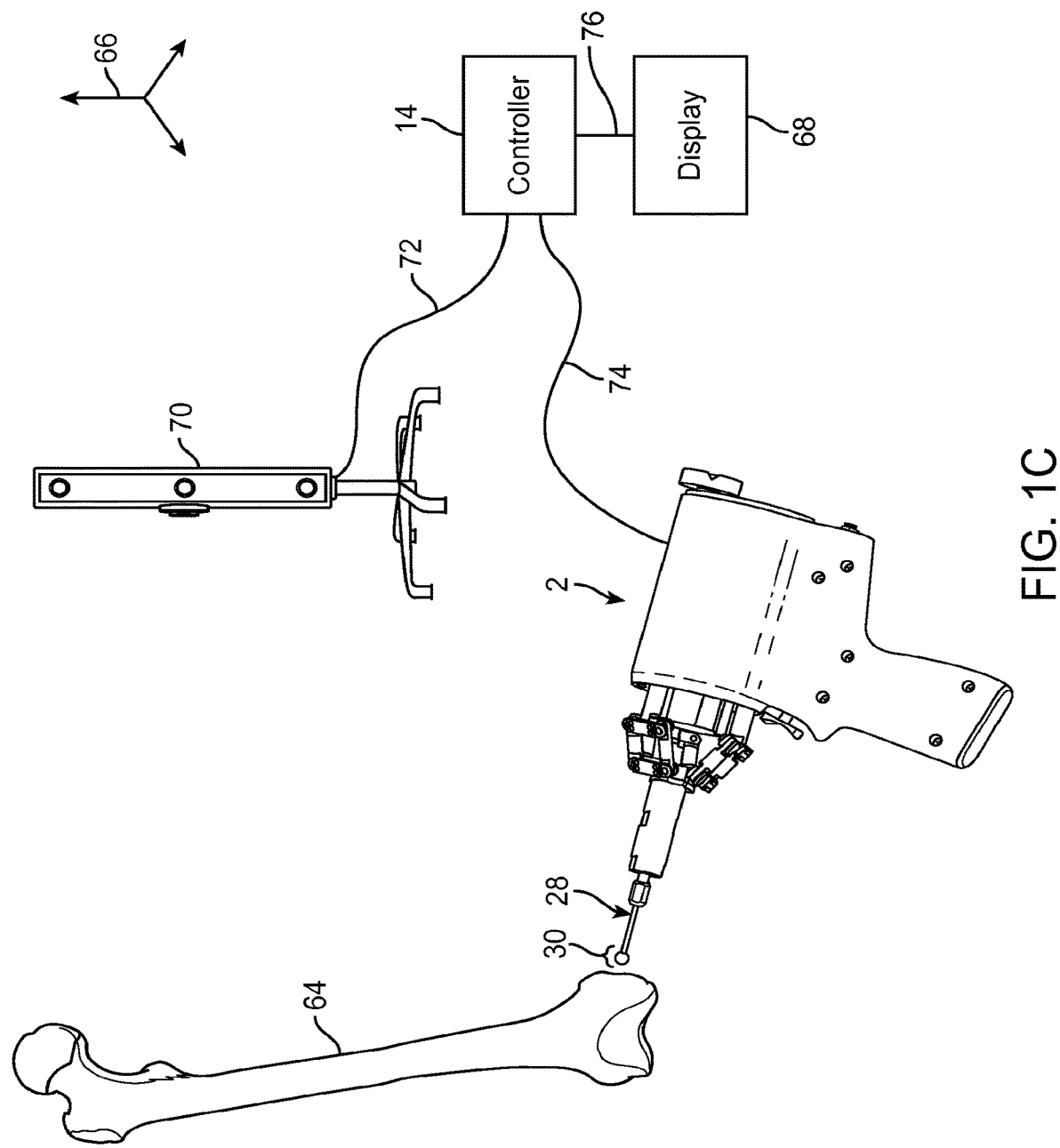
FIG. 1C illustrates an embodiment wherein an optical tracking system is utilized to track one or more of a targeted tissue structure and a cutting tool.

Referring to FIG. 1C, in one embodiment, an optical tracker system (70), such as those available from Northern Digital, Inc. of Ontario, Canada, may be utilized to monitor the real or near-real time position of one or both of the handheld manipulator (2) and bone (64), subject to the requirement that the monitored structures be outfitted with markers (such as groups of small spheres or disks; not shown) that reflect light emitted from the optical tracking system (70). A controller (14), such as a computer, processor, or microcontroller, which may reside, for example, in a personal computer or similar computing apparatus, may be coupled, via electronic leads (72, 72) to the tracking system (70) and handheld manipulator (2), and configured to operate motors within the manipulator (2) to assist with avoidance of bone removal pathways that may be attempted by an operator, as discussed in further detail below. A display (68) may be coupled via another lead (76) to the controller and configured to show an operator a graphical user interface featuring information regarding the subject anatomy and interaction between the anatomy and the subject tools. Any of the leads described herein (for example, 72, 74, 76) may be replaced in other embodiments with wireless connectivity to avoid physical lead tethering.

In other embodiments, other spatial tracking technologies, such as those based upon ultrasonic or ultra-wide-band transducer monitoring (for example, to analyze time-of-flight information for various locations on a handheld manipulator 2), may be utilized to characterize the spatial positioning of a handheld manipulator and associated tool (28) in near real or real time.

Figure 1D:
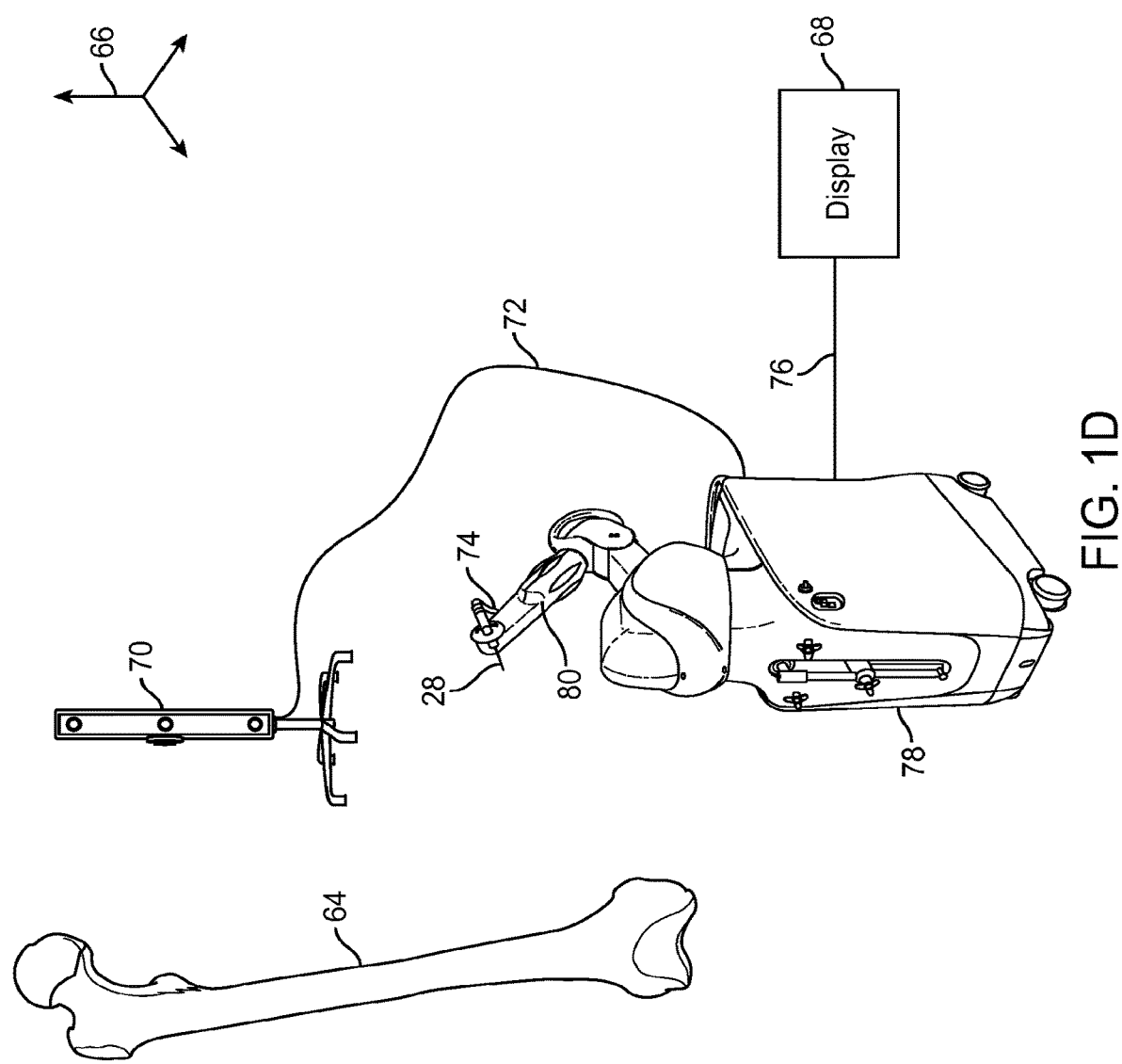
FIG. 1D illustrates an embodiment wherein an optical tracking system is utilized to track one or more of a targeted tissue structure and a cutting tool, which may be coupled to a robotic arm.

Referring to FIG. 1D, another embodiment is illustrated wherein an optical tracking system (70) may be utilized to track the spatial positions of one or more of the subject tissue structure (64) and a robotic arm (80) which may be utilized to support the tool (28) during at least a portion of the surgical procedure. The embodiment of FIG. 1D features a robotic surgery system having a base assembly that comprises a controller (78) which is operatively and driveably coupled to the robotic arm (80) as well as the tool (28). An electronic lead (74) couples the tool (28) with the controller base, another electronic lead (72) couples the optical tracking system (70) with the controller base (78), and another electronic lead (76) couples the controller base (78) to a display (68) configured to show a graphical user interface to an operator, as in systems available from MAKO Surgical Corporation of Ft. Lauderdale, Fla., such as those disclosed in U.S. Pat. No. 8,010,180, which is incorporated by reference herein in its entirety. With the controller base (78) grounded and registered relative to the global coordinate system (66) and markers in place coupled to the subject anatomy (64) as well as the tool (28) and/or a portion of the robotic arm (80), the controller may be utilized to monitor the three-dimensional positions of the tool (28) relative to the anatomy (64) with a high level of precision, and to allow an operator, via controlled active and passive robotic arm (80) joint control activity, to manipulate the tool (28) into desirable positions within the desired bone cutting envelope. One of the possible downsides of such a configuration is the inertial and kinematic overhead associated with having the tool (28) coupled to a relatively large robotic arm (80). In one embodiment, the robotic arm (80) may be configured to compensate, at least in part, for the effects of gravitational acceleration (socalled "gravity compensation), thereby reducing the loads that need be applied in certain directions to move the tool (28). Such gravity compensation may be accomplished using motors and sensors within the intercoupled robotic arm (80), which are capable of monitoring the positioning of the arm (80) and intercoupled tool relative to the acceleration of gravity, and counteracting the effects of gravity upon the arm and tool. Gravity compensation mechanisms such as the depicted robotic arm configuration (80), or such as more simplistic mechanisms such as gravity-countering linear or nonlinear spring mechanisms, may be applied in the embodiments described in reference to FIGS. 1E and 1F as well.

Referring to FIG. 1E, another embodiment is depicted wherein a handheld manipulator (2) may be utilized in a tissue structure (64) intervention, and wherein the spatial positioning of the bone (64) and manipulator (2) may be monitored using two mechanical tracker assemblies (90, 92), each of which has a proximal end coupled to a base structure (82, 84) that has a known position and orientation relative to a coordinate system such as the global coordinate system (66) of the operating room. The distal end of the first tracker assembly (90) is coupled to the bone (64) using a bone coupling member which may be fastened to the bone with one or more pins as shown, and removably coupled to the distal portion of the tracker assembly (90) with a coupling interface (122) that may comprise a kinematic quick connect fitting or interface, as described in further detail below, and also in U.S. patent application Ser. No. 13/276,048, filed simultaneously, which is incorporated by reference herein in its entirety. A similar coupling interface (124) may be utilized to couple the proximal end of the mechanical tracker (90) to the base structure (82). As described in the aforementioned incorporated by reference disclosure, the depicted mechanical tracker (90) embodiment may comprise four joints (100, 102, 104, 106) and three elongate members (94, 96, 98), as well as sensors configured to monitor the rotations of the joints (100, 102, 104, 106). A similar second mechanical tracker (92) comprising four joints (114, 116, 118, 120), three elongate members (108, 110, 112), and similar joint rotation sensors may be utilized to track the position and orientation of the handheld manipulator (2). Electronic leads (88, 86) from the trackers (90, 92) may be utilized to allow the controller (14) to process the pertinent signals and calculate, as well as display (68), the relative spatial positions and orientations of the subject tissue structure (64) and tool (28) relative to each other. Further, as described in greater detail below, motors within the handheld manipulator (2) may be controllably actuated to provide motion compensation to at least partially defeat certain aberrant motions (i.e., aberrant because they stray from a predetermined desired cutting envelope) attempted by virtue of manual commands placed upon the handheld manipulator.

Figure 1F:
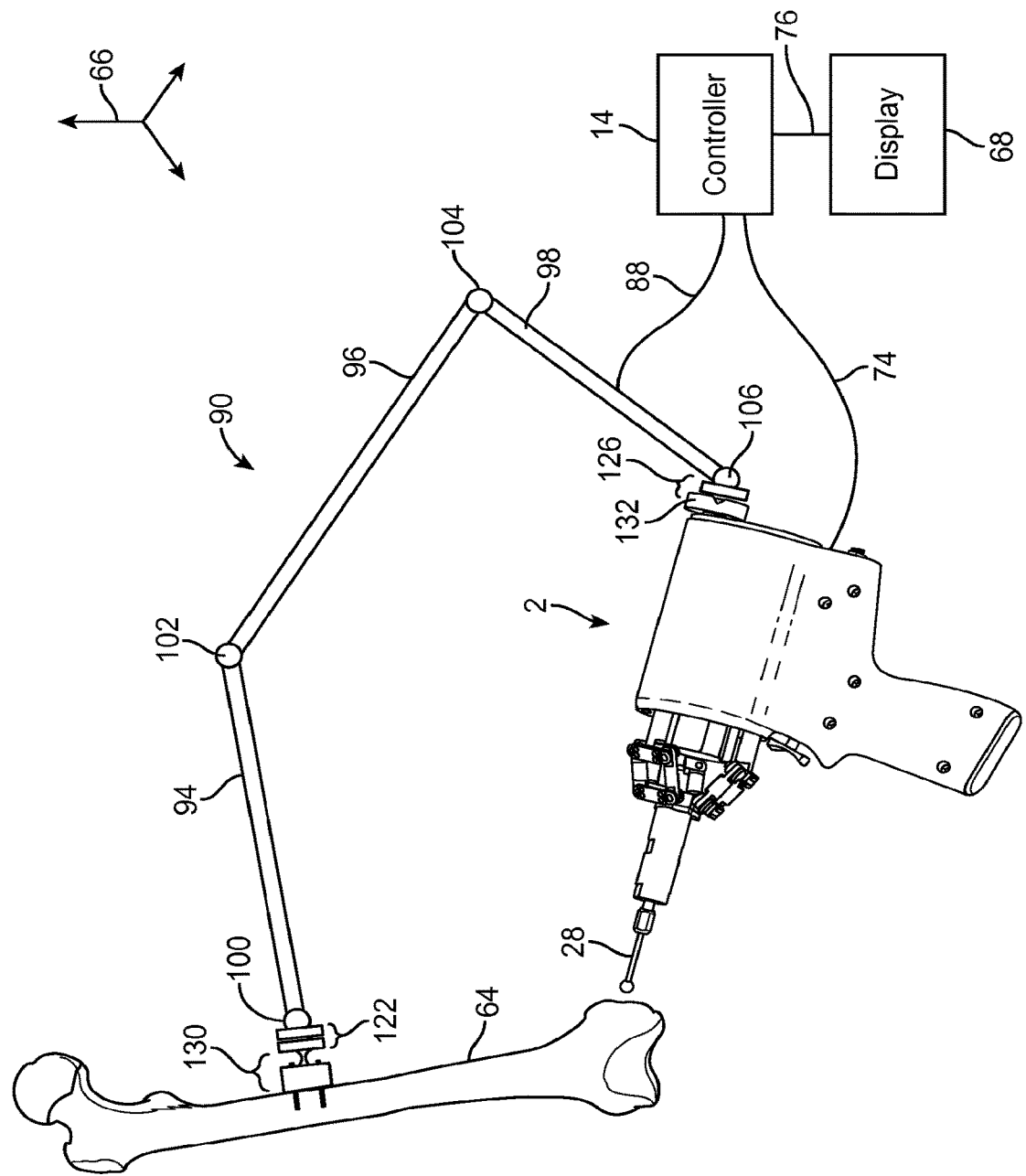
FIG. 1F illustrates an embodiment wherein a mechanical tracker linkage is utilized to monitor the spatial relationship between a targeted tissue structure and an interventional tool.

Referring to FIG. 1F, in another embodiment, a single mechanical tracker (90) may be utilized to track the positions and/or orientations of the manipulator (2) and tool (28) relative to the subject anatomy (64), with inherent registration by virtue of the connectivity between the two elements. The proximal end of the mechanical tracker (90) may be coupled to a coupling interface member (132) of the handheld manipulator (2) using a removably attachable kinematic quick connect interface; similarly, the distal end of the mechanical tracker (90) may be coupled to the bone coupling member (130) with a removably attachable kinematic quick connect interface.

With each of the embodiments shown in FIGS. 1C-1F, the controller (14) may be utilized along with the various position/orientation sensing elements, to monitor the three dimensional spatial relationships of the subject anatomy and manipulator/tools. This understanding may be harnessed in a motion compensation configuration wherein attempted (either purposefully or accidentally) tool movement commands manually at the manipulator may be at least partially defeated using electromechanical features of the manipulator to keep the tool on track and within a previously determined desired tissue cutting envelope. In other words, an aspect of closed loop control may be employed to keep the tool within the prescribed bounds.

Figure 2B:
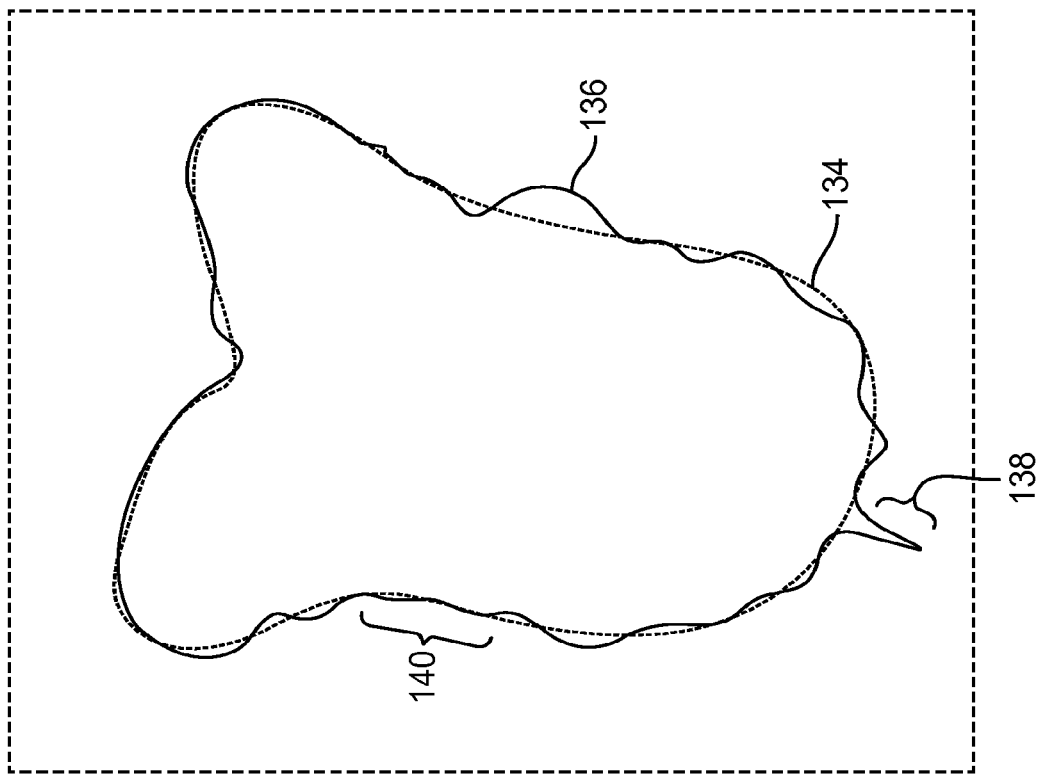
FIG. 2B illustrates one variation of an attempted cutting envelope relative to a tissue substrates and desired bone cutting envelope.
Figure 2A:
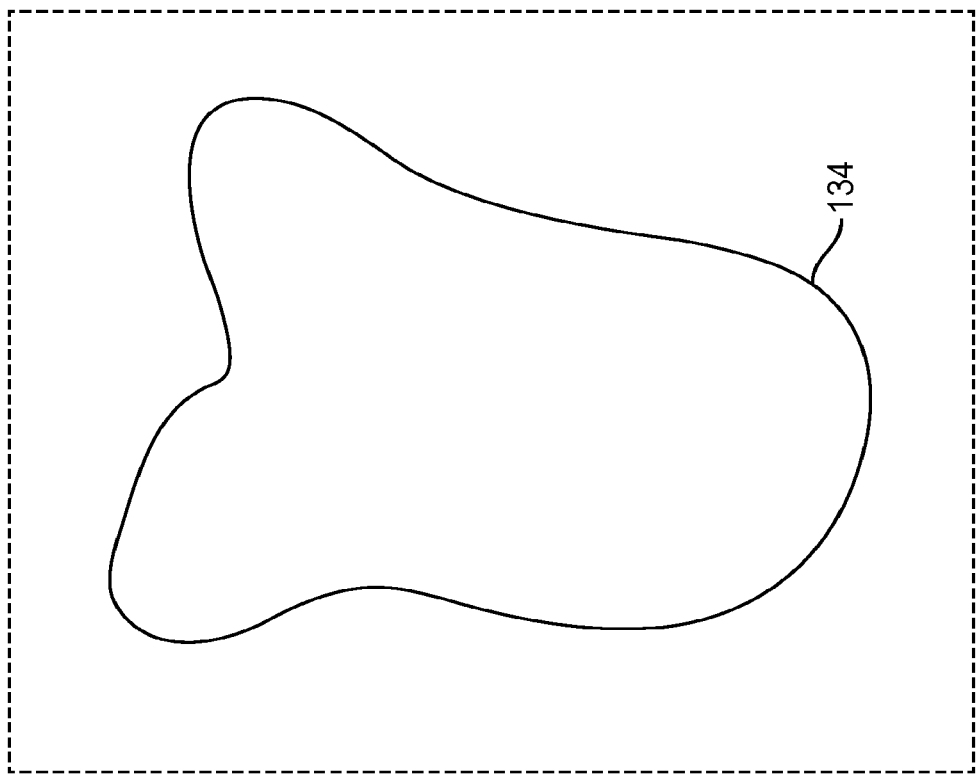
FIG. 2A illustrates a desired bone cutting envelope relative to a tissue substrate.

For example, referring to FIG. 2A, a desired bone cutting envelope (134) is illustrated. Such a bone cutting envelope (134) may, for example, represent a volume of bone to be removed based on preoperative planning with regard to the patient's anatomy and an orthopaedic resurfacing prosthesis of particular geometry. In an ideal world, an operator would be able to utilize a manipulator such as a handheld manipulator to sculpt precisely within the bone cutting envelope (134) so that the prosthesis fits precisely against the prepared bony surface. In actuality, various factors may affect an operator's ability to command the tool precisely within the desired bone cutting envelope (134), such as tremors of the operator (which tend to occur at relatively high frequencies, such as frequencies greater than about 1 Hz (for example, frequencies between about 1 Hz and about 12 Hz), and at relatively low amplitudes) and/or accidental or unplanned bulk motions of the operator or the patient (which tend to occur at relatively low frequencies, such as frequencies below 1 Hz, and at various amplitudes, including relatively high amplitudes).

For example, referring to FIG. 2B, a desired bone cutting envelope (134) is shown with a dashed line, and an actual commanded tool path (136) is shown with a solid line. Small tremor-like activity is illustrated, for example, with the relatively low amplitude, and relatively high frequency, departures (140) from the desired bone cutting envelope (134). An accidental bulk motion of the patient or operator is illustrated (138) as a relatively high amplitude, lower frequency aberration or departure from the planned envelope (134). To address commands such as these which, absent some mitigation, would take the tool outside of the desired bone cutting envelope (134), a controller may be configured to react to such commands quickly by automatically moving the tool back toward, and preferably back within, the preferred bone cutting envelope (134). FIGS. 3A-3M illustrate aspects of a handheld manipulator system configured to not only deflect the tool controllably in pitch and/or yaw relative to a longitudinal axis (142) of the tool (28), but also to insert or withdraw the tool substantially parallel to that axis (142).

In one embodiment, a controller may be configured to modulate the cutting velocity of a cutting tool, such as an angular velocity of a rotary bone cutting burr, or the oscillatory velocity and/or frequency of a reciprocating cutting tool, such as a reciprocating bone saw, based at least in part upon the location of the tool relative to the desired bone cutting envelope. For example, in one embodiment, the controller may be configured to generally reduce the angular velocity, oscillatory velocity, or oscillatory frequency of the cutting tool when the tool is moved adjacent an edge of the desired bone cutting envelope. In another embodiment, a controller may be configured to modulate the cutting velocity (i.e., angular velocity, oscillatory velocity, or oscillatory frequency) of the cutting tool based at least in part upon the location of the tool within a predetermined workspace for the handheld manipulation. In other words, the controller may be configured such that the angular velocity, oscillatory velocity, or oscillatory frequency is generally reduced when the tool is moved toward the edge of the predetermined workspace.

Figure 3A:
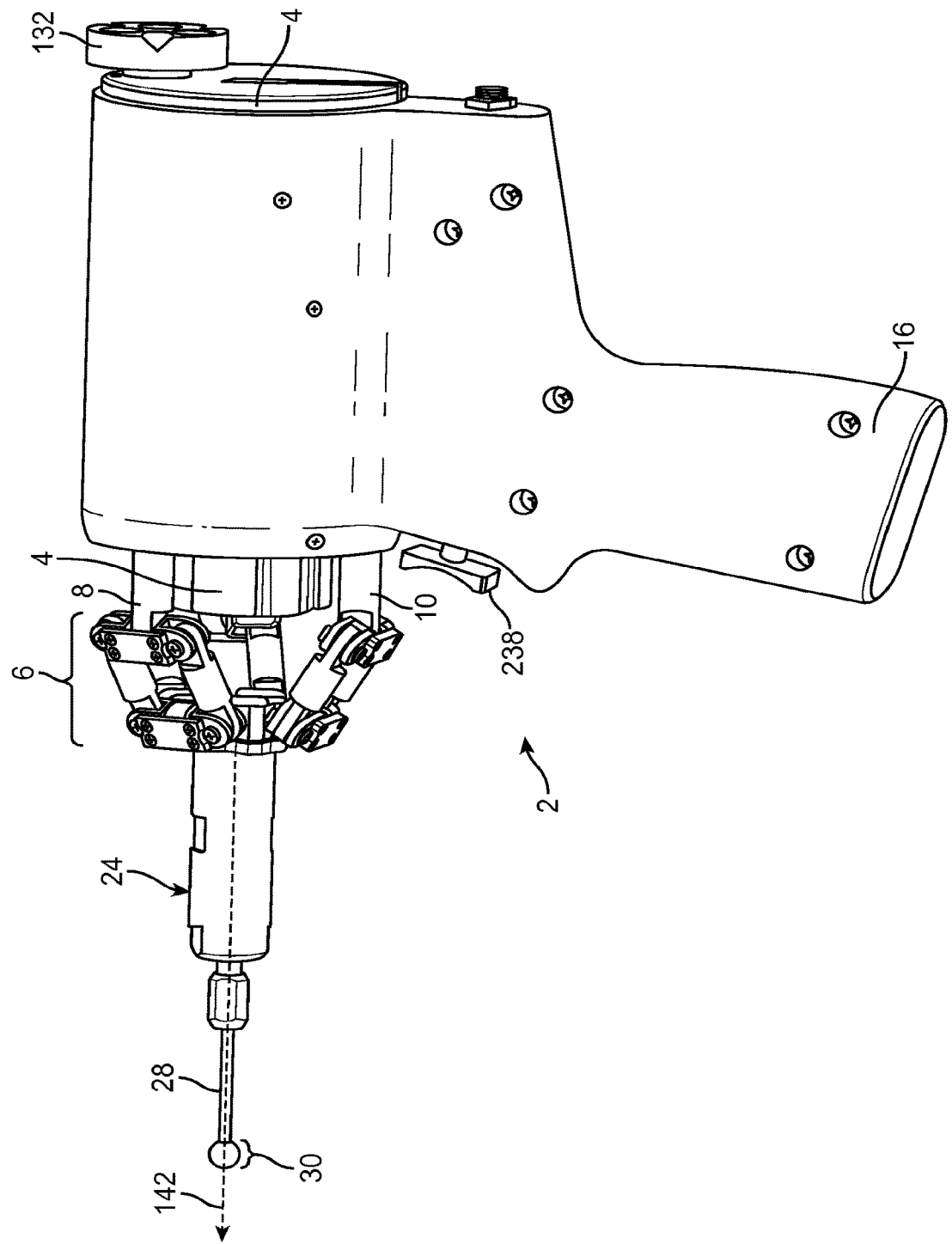

Referring to FIG. 3A, a side view of a handheld manipulator (2) configuration is depicted, wherein a frame assembly (4) extending through a housing (16) has a proximal coupling interface member (132) configured to be easily couplable to a mechanical tracker or other member. Extending distally of the housing (16) are three elongate structural members (two shown—8, 10; shown in other figures—12) which are coupled to a motion compensation assembly (6), which is coupled to a tool drive assembly (24). The tool drive assembly (24) may comprise a motor and motor housing or motor coupling structure, and is movably coupled to the tool (28). Upon manual depression of the trigger (238) operatively coupled to the housing (16), a motor of the tool drive assembly (24) may cause the tool (28) or the end effector portion thereof (30; such as a bone burring tip) to rotate at a controlled angular velocity selected to remove bony material from a substrate. FIG. 3B illustrates a different orthogonal view of the assembly of FIG. 3A, to illustrate that the motion compensation assembly (6) and associated elongate structural members (two shown—8, 10; shown in other figures—12) and assemblies related thereto, may be utilized to controllably insert/retract (144) and/or pitch and or yaw the tool (28) omnidirectionally (146, 148, 150) in response to controlled activity of associated actuators. The combination of insertion/retraction control (can also be called "z-axis" control given a z-axis coaxial with the longitudinal axis 142 of the tool), pitch/yaw control, roll control with the motor (24) configuration, and x and y axis (relative to the z-axis) control with the frame linkage (6) assembly provides 6-degree-of-freedom controlled movement at the end effector tip portion (30), and therefore 6-degree-of-freedom motion compensation under the paradigms described herein.

Figure 3C:
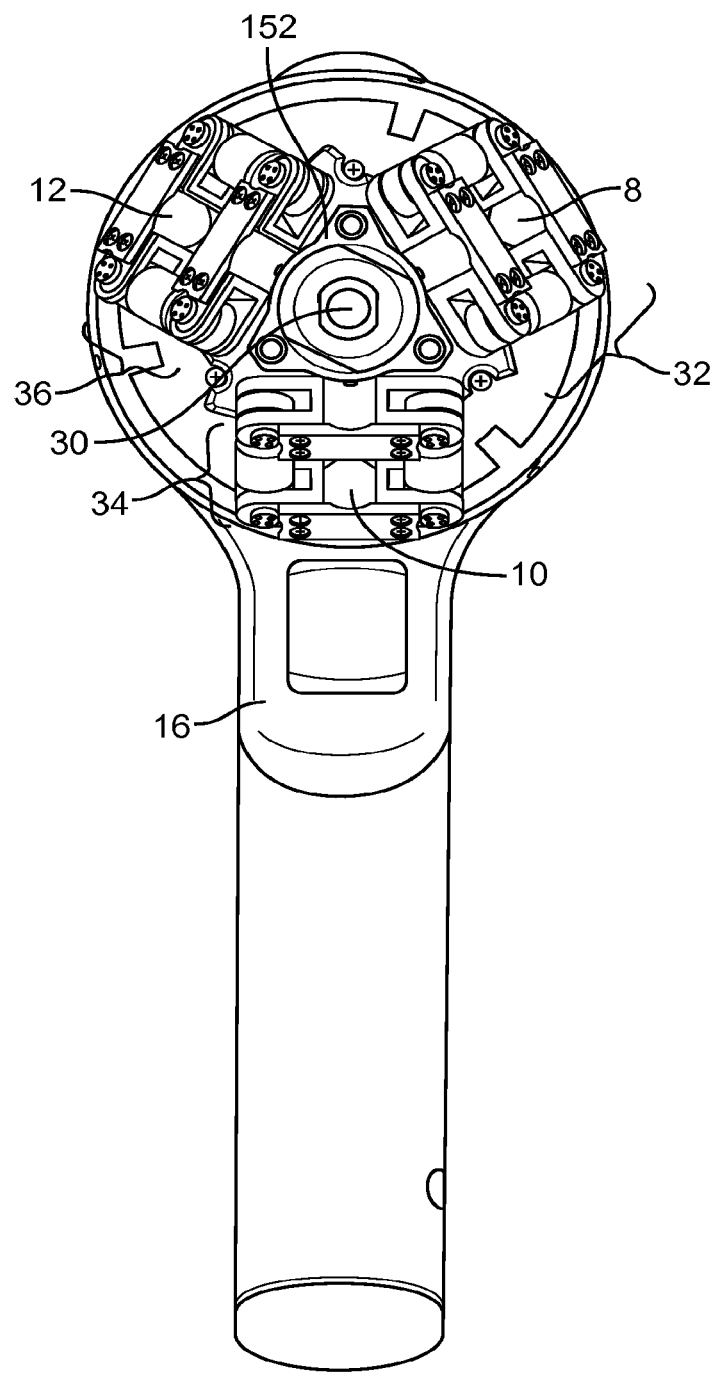
Figure 3G:
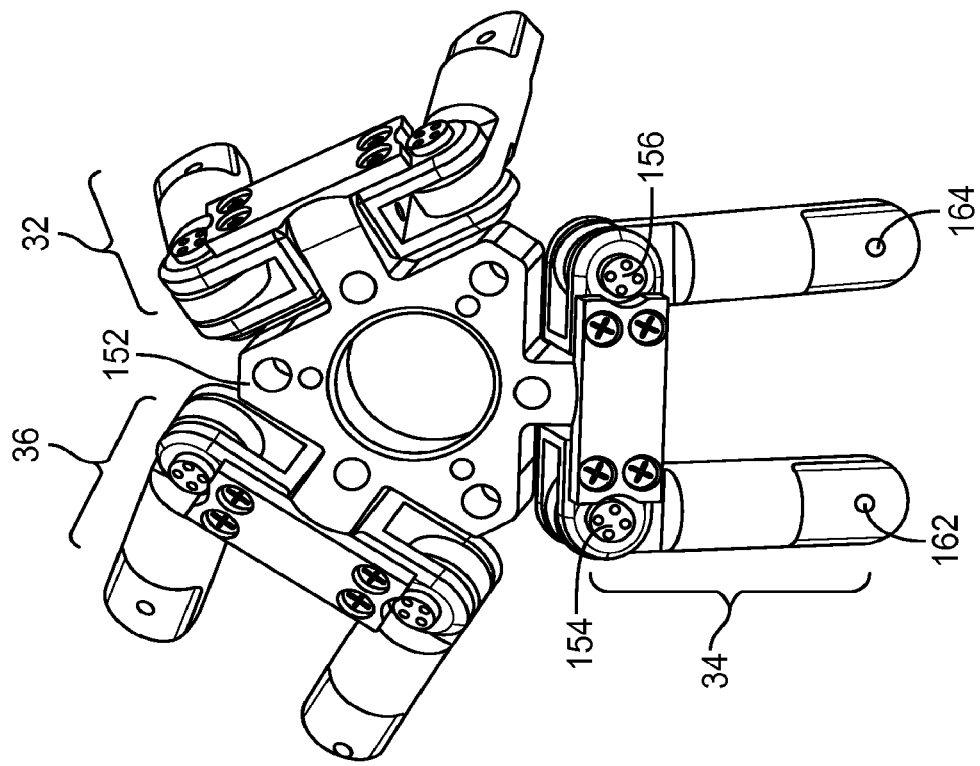

Referring to FIG. 3C, another orthogonal view illustrates the third elongate structural member (12), along with a motion compensation coupling base (152) that is movably coupled to each of three motion compensation linkage assemblies (32, 34, 36) that are coupled to the elongate structural members (8, 10, 12). FIG. 3D shows the housing (16) deconstructed from the rest of the handheld manipulator assembly. FIG. 3E shows the frame assembly (4) that fits inside of the housing (16) of FIG. 3D, the frame assembly comprising three motors operatively coupled to the three elongate structural members (8, 10, 12) and configured to controllably and independently retract or insert these members in response to motion compensation commands from the controller (14), which may be combined through the motion compensation assembly (6) to omnidirectionally pitch/yaw the tool, as well as simultaneously insert or retract the tool.

Figure 3F:
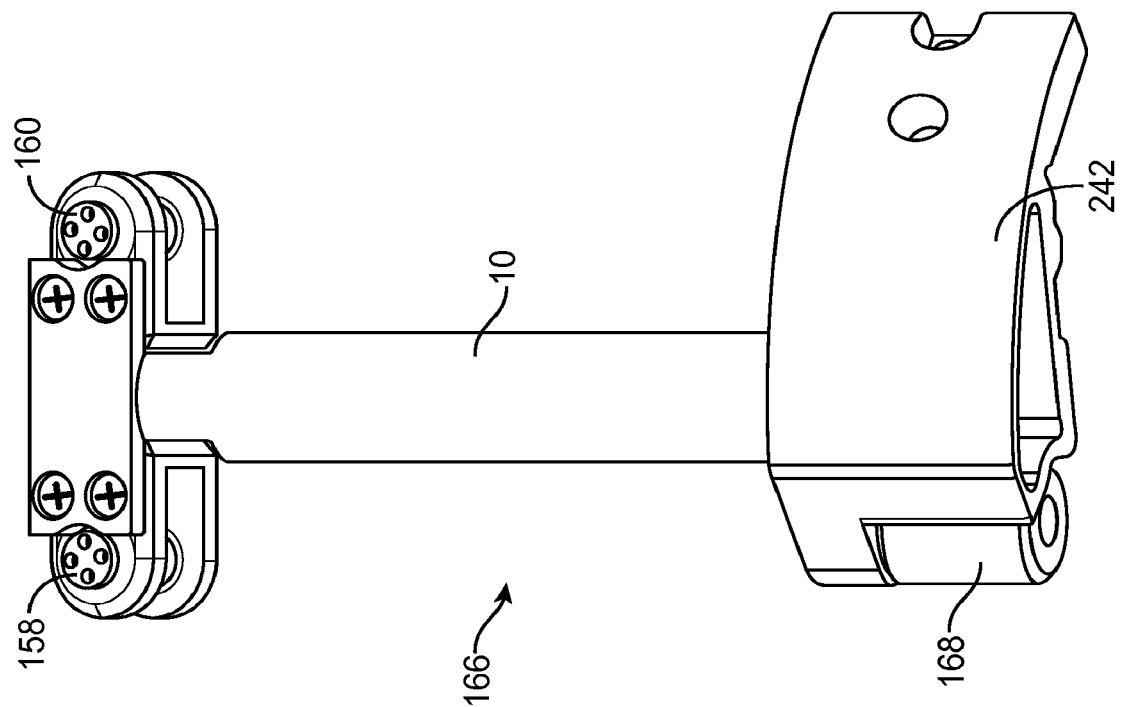
Figure 3H:
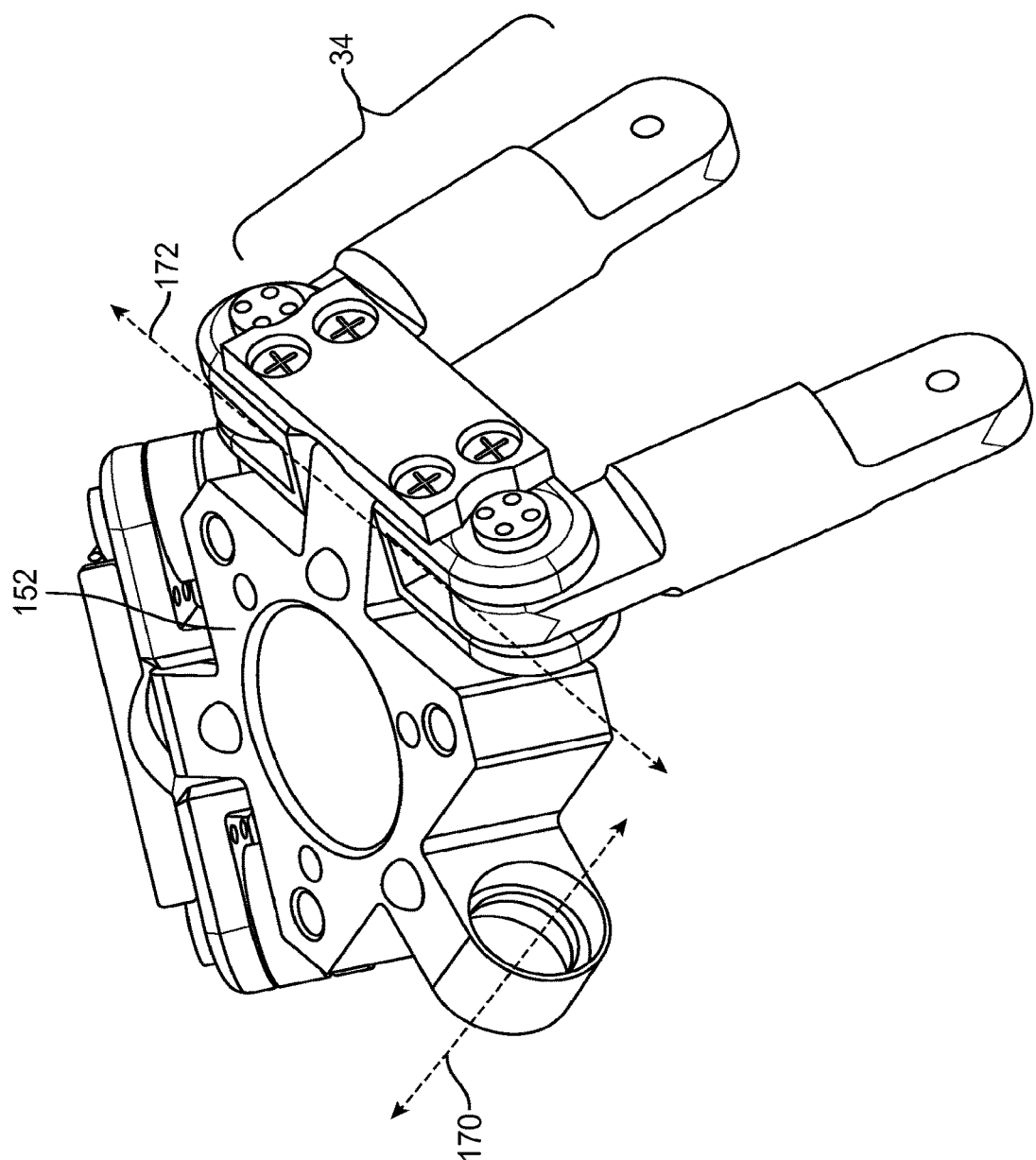

Referring to FIG. 3F, each of the elongate structural members (10); not shown are identical subassemblies for 8 and 12) is coupled into a movable lead screw assembly (166) comprising a threaded member (168) that moves the elongate member (10) and guide base member (242) axially relative to a screw that is threaded through the threaded member (168) and controllably twisted in one of two directions by an associated motor, to either insert or retract the elongate member (10). The distal portion of the movable lead screw assembly (166) comprises two rotatable coupling interfaces (158, 160) configured to be interfaced with two apertures (162, 164) formed in the paired motion compensation linkage (34), which has two additional similar rotatable coupling interfaces (154, 156). The relative motion provided by the linkages (32, 34, 36) assist in facilitating omnidirectional motion at the motion compensation coupling base (152), which is fixedly coupled to the tool drive assembly (24). FIG. 3H shows a different view of the assembly of FIG. 3G with the exception that one of the motion compensation linkage assemblies (36—not shown) has been removed to illustrate that a rotational degree of freedom is provided in the linking with the motion compensation coupling base (152), as shown, for example, with the two illustrated axes of rotation (170, 172) for two of the motion compensation linkage assemblies (36—not shown, 34 shown).

Figure 3I:
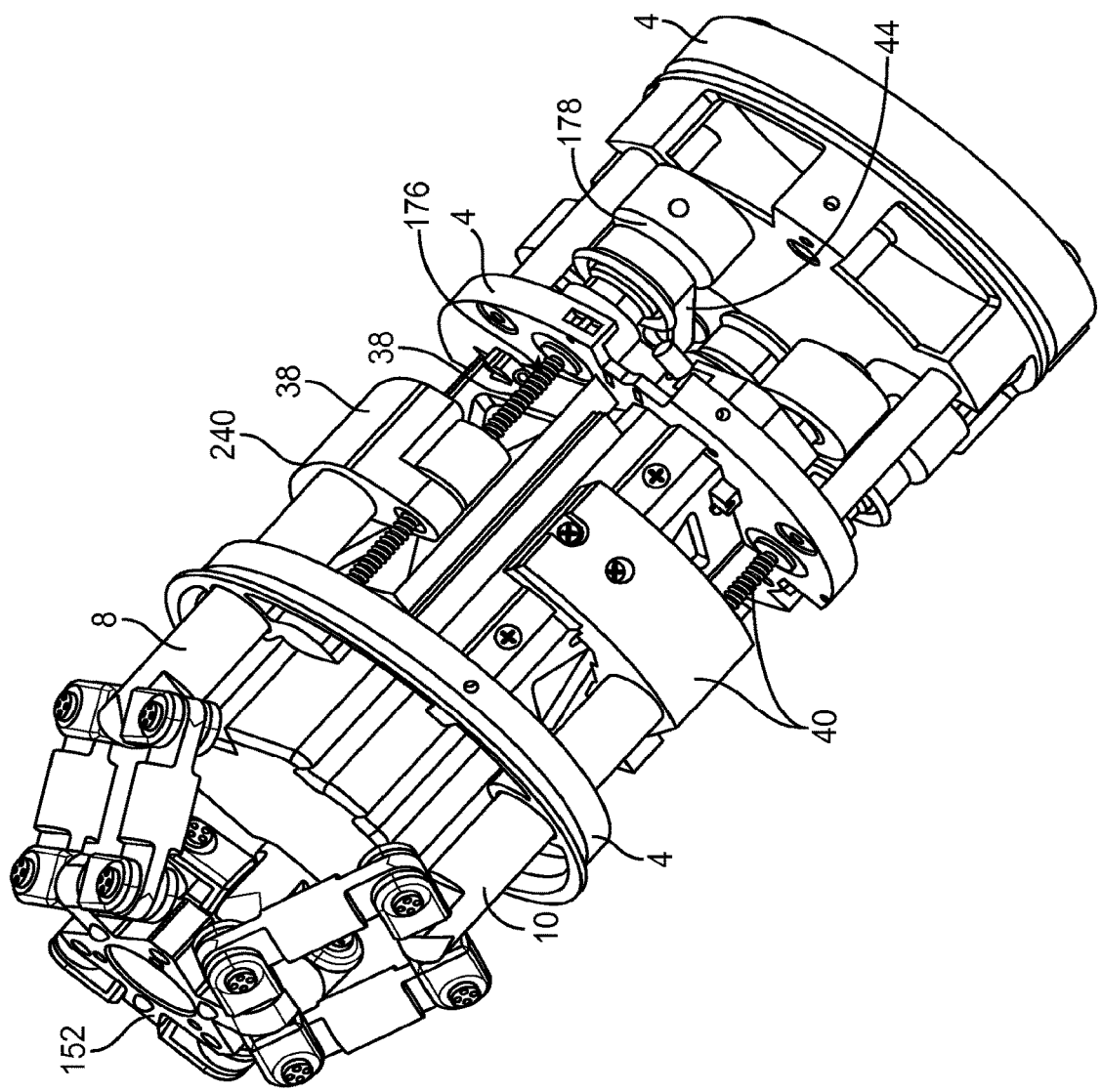
Figure 3J:
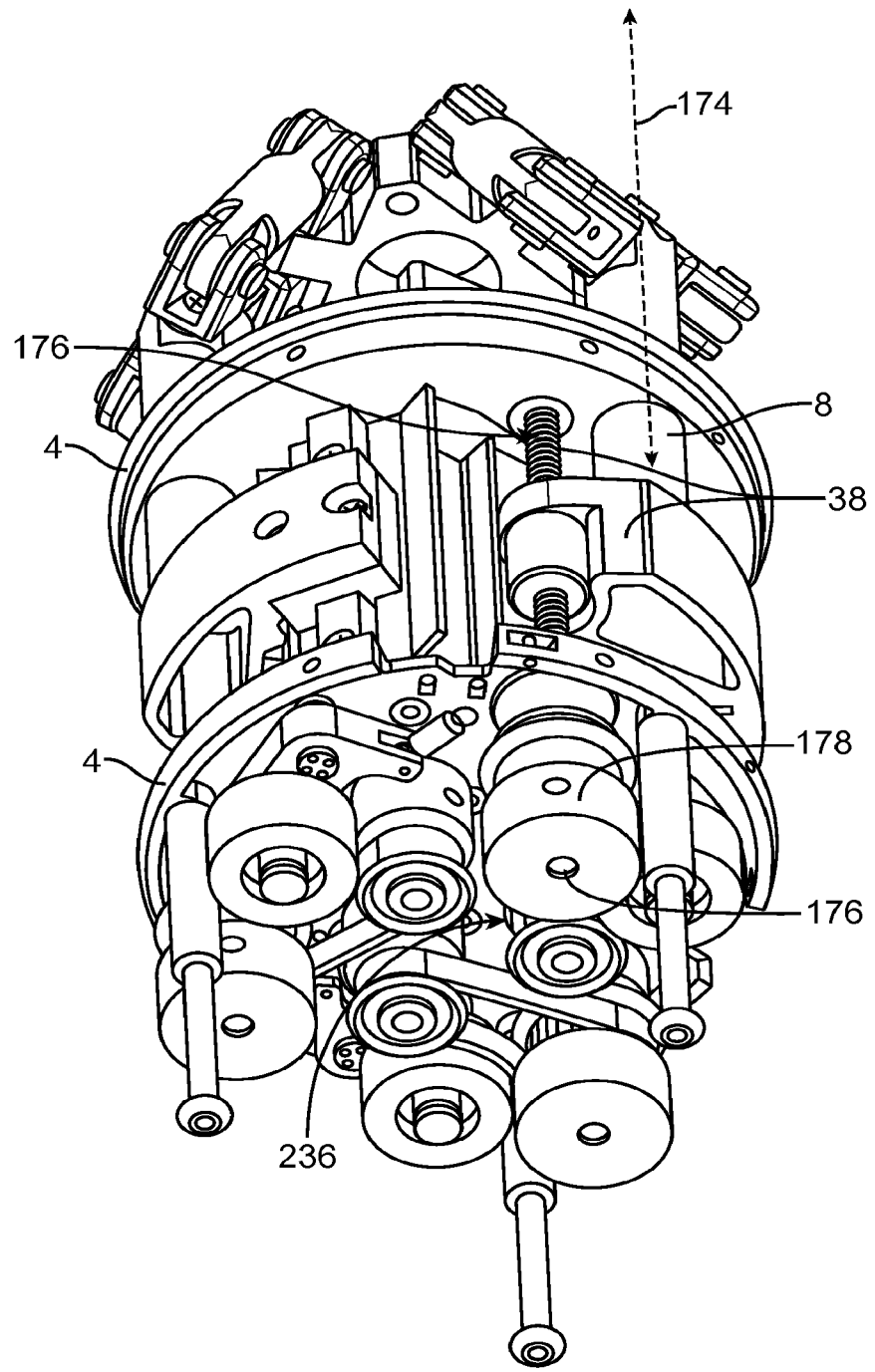
Figure 3K:
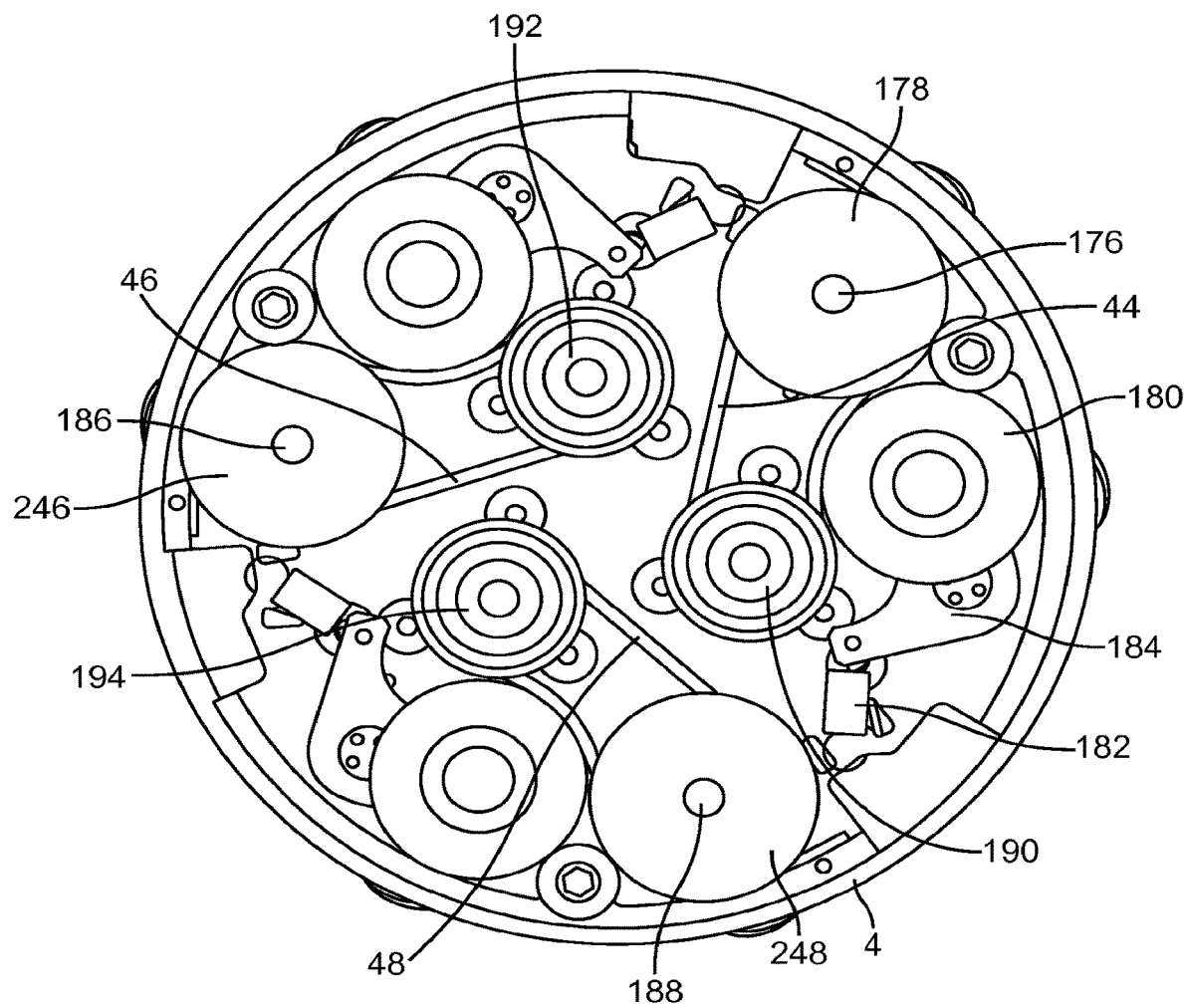
Figure 3M:
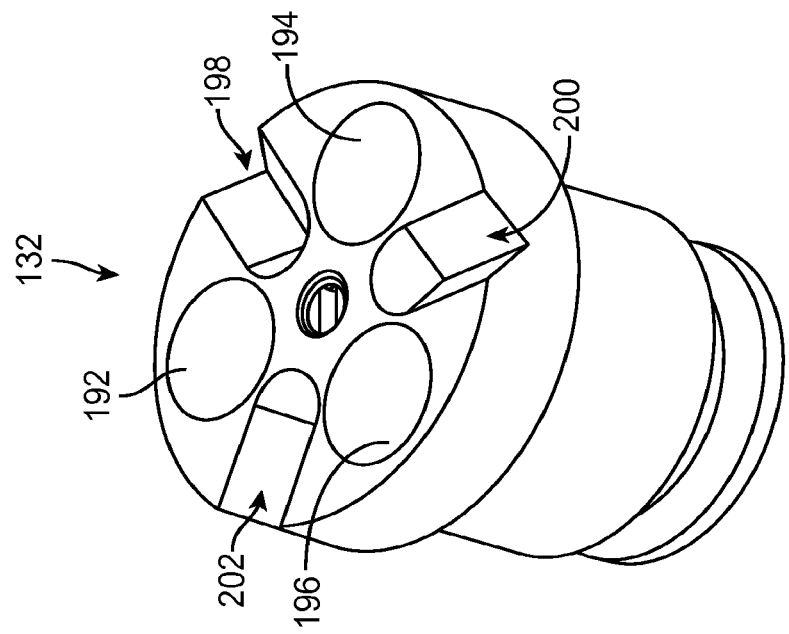

Referring to FIG. 3I, a frame assembly (4) is shown with all three elongate structural members (8, 10, 12) movably coupled thereto. A first lead screw assembly (38) comprises the first elongate structural member (8), the first guide base member (240), and a first lead screw (176) that is coupled to a first driven pulley (178) movably coupled to a motor (not shown) by a first belt (44). FIG. 3J shows a partial assembly of the more complete assembly of FIG. 3I to illustrate the screw (176), driven pulley (178), and motorized insertion/retraction (174) provided by the motor (236) that drives the belt and associated driven pulley (178) in one of two directions subject to electronic commands from a controller (14). FIG. 3K shows a bottom view to illustrate that there are three similar mechanisms to independently and simultaneously control insertion or retraction of each of the three elongate structural members (8, 10, 12), and therefore, as described above, provide omnidirectional pitch/yaw as well as insertion/retraction of the motion compensation coupling base (152) and associated tool drive assembly (24) and tool (28). Three motors (not shown), which may be equipped with gearboxes, underly each of three motor pulleys (190, 192, 194). Each of the motor pulleys is coupled to a driven pulley (178, 246, 248) using a belt (44, 46, 48), and each driven pulley (178, 246, 248) is coupled to a lead screw (176, 186, 188). Each lead screw (176, 186, 188) is coupled to a threaded member, guide base member, and elongate structural member such that rotation of each motor causes rotation of the lead screw and insertion or retraction of the pertinent elongate structural member.

In another embodiment, one or more of the belt drive rotary motion transfer configurations shown in the embodiment of FIGS. 3I-3K may be replaced with a gear to gear mechanical interface (i.e., a "gear drive" configuration as opposed to a "belt drive" configuration), wherein a drive belt is avoided in each gear drive interface by having direct mechanical teeth interfacing. The belt drive configurations may be desired for the mechanical and acoustic damping that accompanies a belt drive interface, as well as the geometric efficiency afforded by belt drive interfaces, wherein driving and driven capstans may be separated and remain driveable coupled without geartrains therebetween to bridge geometric gaps. Any transmission means described herein may be replaced in an alternate embodiment with a different transmission means, with the same purpose of transferring motor torque to the lead screws (or other) actuations members.

Figure 3L:
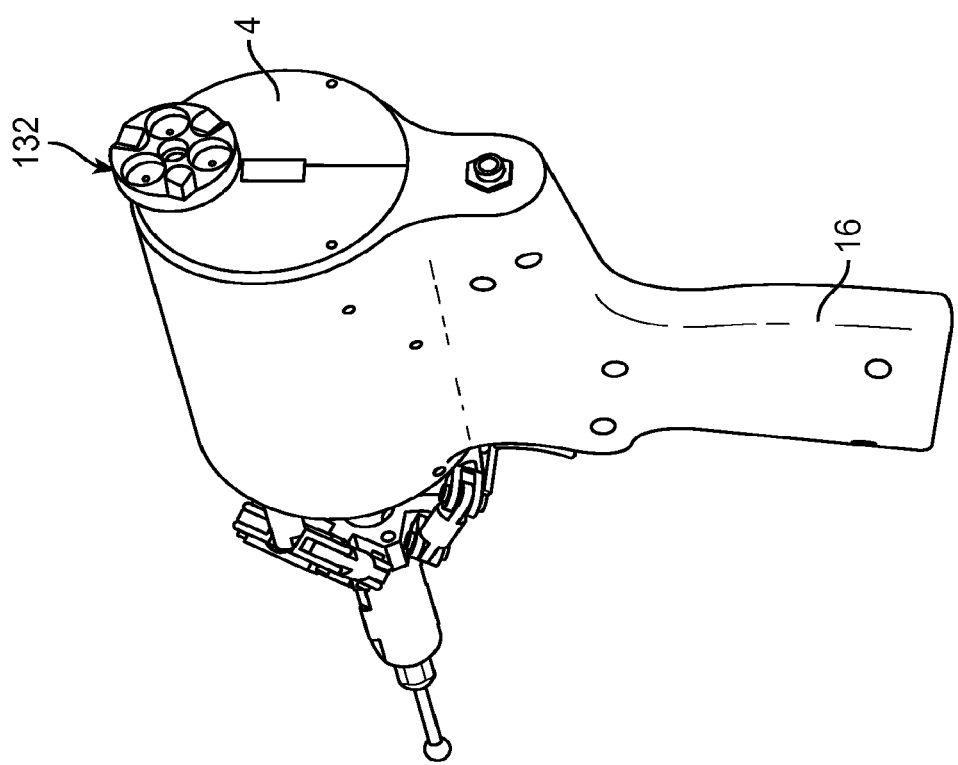

Referring to FIG. 3L, the proximal coupling interface member (132), as well as other coupling interface members (see, for example, the interfaces 122, 124, 126, 128) may comprise a kinematic quick connect fitting, as described in the aforementioned incorporated by reference disclosure, which comprises one or more magnetic elements (192, 194, 196) which may have polarities organized to only allow one orientation, and to also facilitate a relatively simple disconnect via a relatively small, high-impulse load applied to the interface. One or more valley features (198, 200, 202) assist in providing a kinematic interface only capable of one predictable orientation.

Figure 4A:
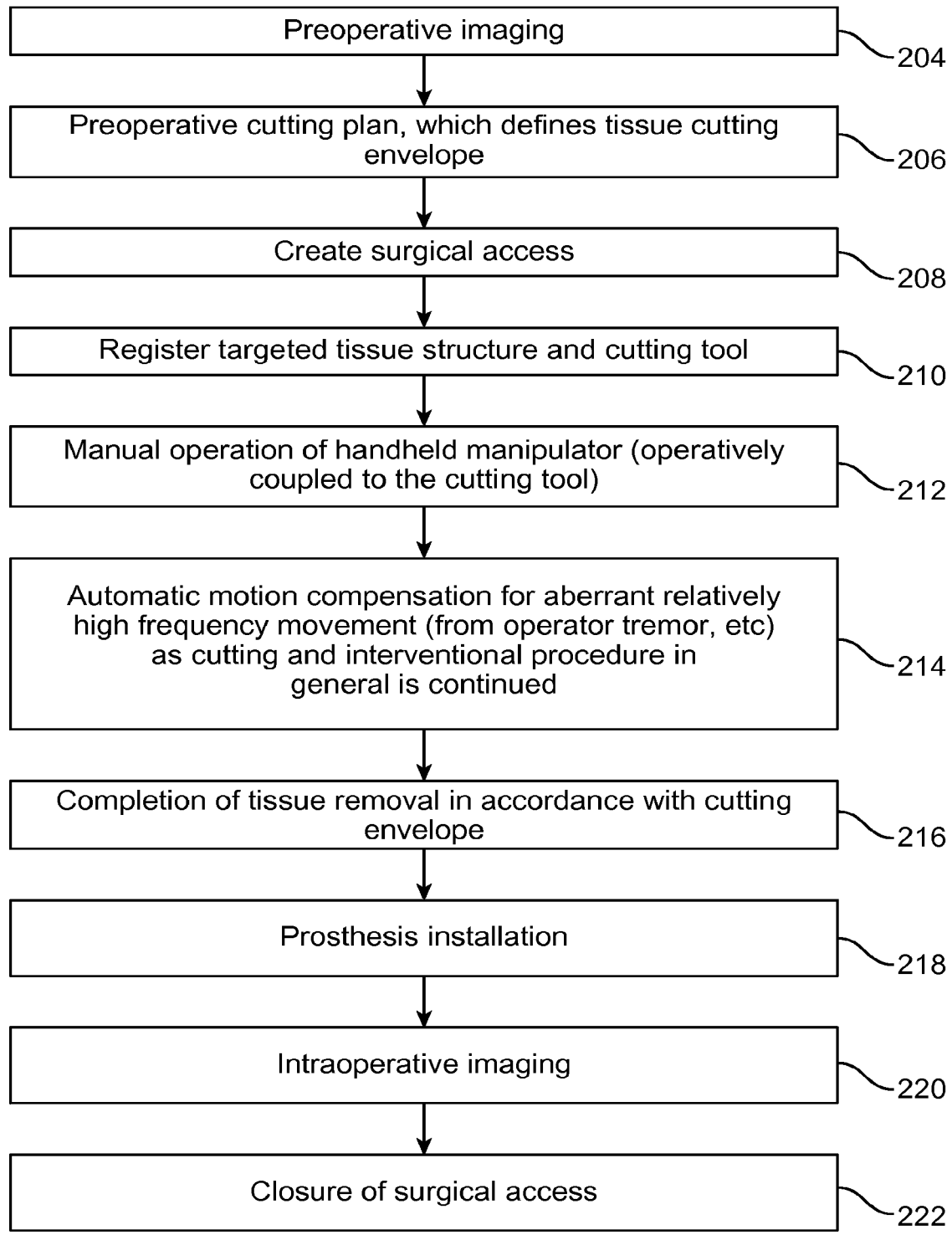
FIGS. 4A-4C illustrate aspects of process embodiments wherein a motion-compensated interventional tool may be utilized in a surgical procedure.

Referring to FIGS. 4A-5C, various processes for utilizing the subject configurations in surgery are illustrated. As shown in FIG. 4A, after preoperative imaging (such as computed tomography, radiography, ultrasound, magnetic resonance, or other medical imaging) (204), a preoperative cutting plan may be created, and this may define a desired tissue cutting envelope (206). Surgical access may be created (208), the targeted tissue structure and cutting tool registered (210) relative to a coordinate system, and a manipulator operated to cut and/or remove portions of bone or other tissue (212). During such operation, a controller may be configured to monitor the positioning of the bone and cutting tool, to detect aberrant relatively high-frequency movement commands from the operator (i.e., such as those that may come from tremor activity of the operator), and to continue cutting while also defeating at least portions of such aberrant commands, to facilitate keeping the cutting tool within the envelope (214). After tissue removal has been completed in accordance with the cutting envelope (216), a prosthesis, such as a joint resurfacing prosthesis, a screw, or other prostheses, may be installed (218). Intraoperative imaging, such as fluoroscopy, radiography, ultrasound, computed tomography, and/or magnetic resonance may be conducted to confirm positioning of various structures (220), and the surgical access may be closed (222).

In another embodiment, the preoperative cutting plan and definition of a tissue cutting envelope may be conducted without preoperative imaging; instead, the positioning and geometry of the bone and other associated tissue may be determined using non-imaging spatial characterization techniques. For example, in one variation, the spatial positioning of a series of bony anatomic landmarks may be determined using a probe operatively coupled to a system capable of establishing probe positions relative to a global or local coordinate system, such as a robotic arm 80 as described above, and based upon this determination and assumptions about the shape the various tissue structures in between the landmark points (i.e., from previous patient data and/or other related anthropomorphic data), the positioning and geometry of the subject tissue structure (such as a long bone) may be characterized with precision.

Figure 4B:
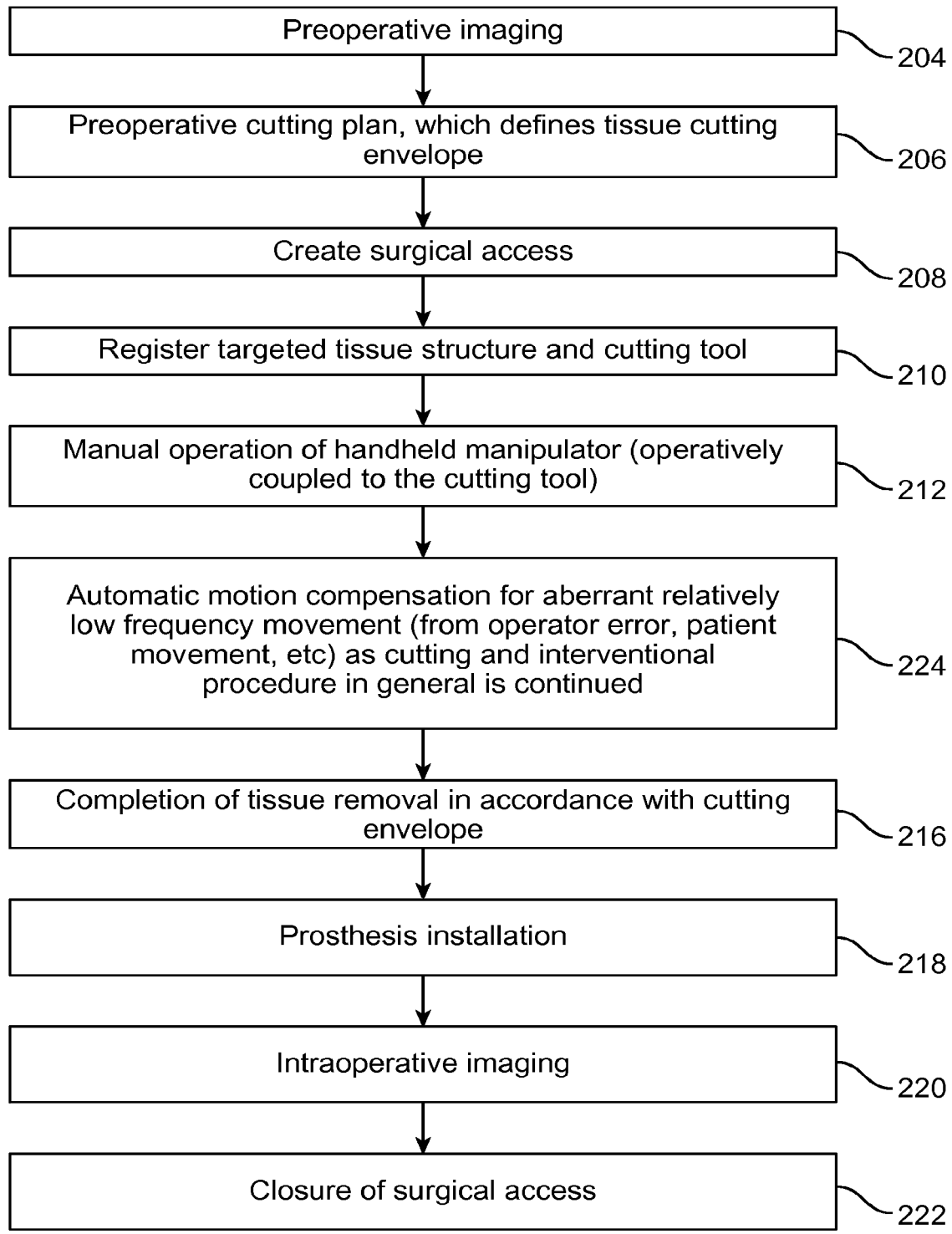

Referring to FIG. 4B, an embodiment similar to that of FIG. 4A is depicted, with the exception that a controller is configured to conduct automatic motion compensation for aberrant commands of relatively low frequency (i.e., such as accidental commands that may result from operator error, patient movement, etc), while the cutting and interventional procedure in general is completed (224).

Figure 4C:
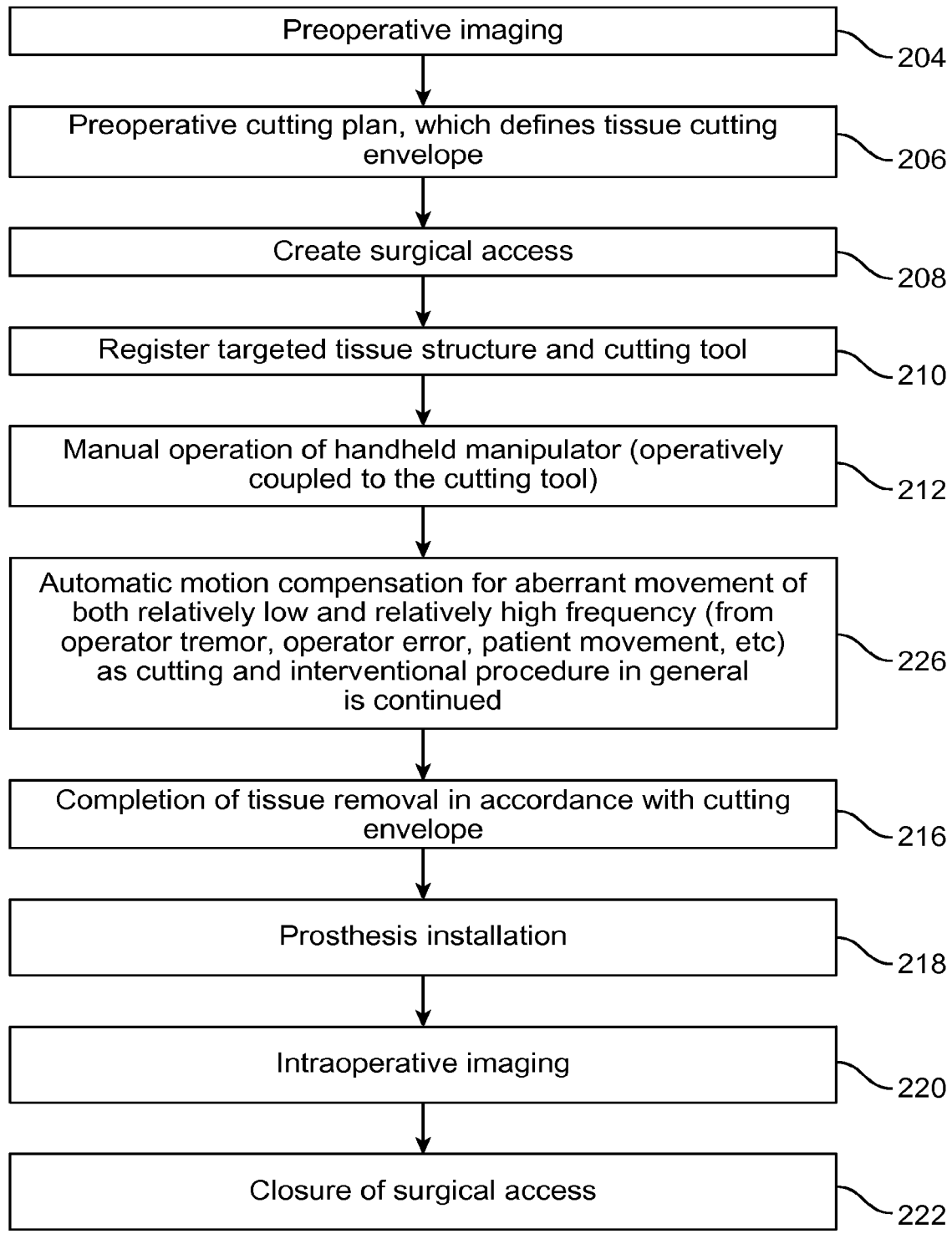

FIG. 4C illustrates an embodiment that combines the functionalities of the embodiments of FIGS. 4A and 4B, such that the controller is configured to conduct motion compensation for both relatively high, and relatively low frequency aberrant commands (226), to facilitate keeping the cutting tool within the desired bone cutting envelope.

Figure 5A:
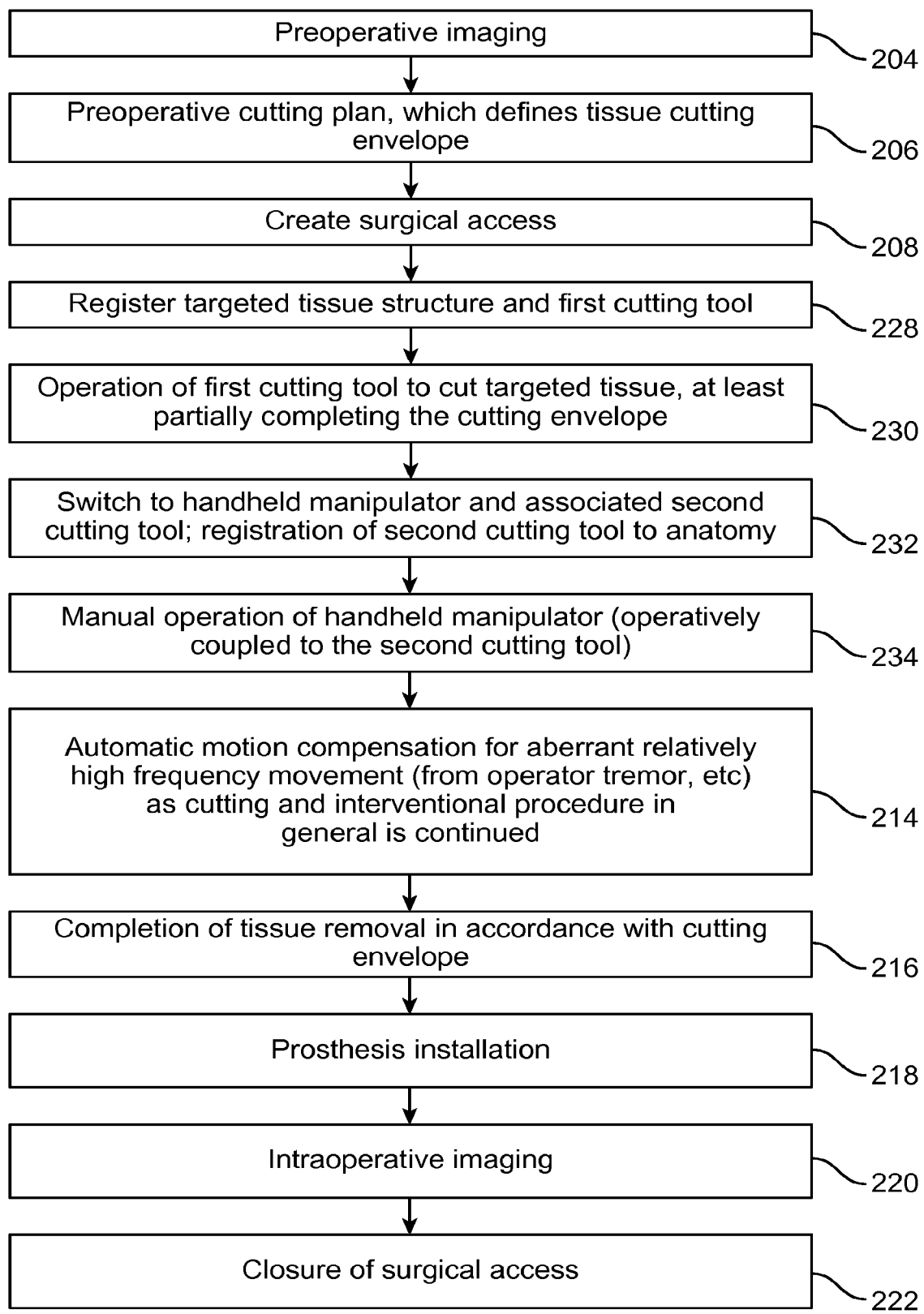
FIGS. 5A-5C illustrate aspects of process embodiments wherein a motion-compensated interventional tool may be utilized in a surgical procedure.

Referring to FIG. 5A, an embodiment is illustrated wherein some steps are similar with the embodiments of FIG. 4A, with the exception of a switching from a first cutting tool to a second cutting tool, with motion compensation for the second tool utilized, which in the illustrative case is part of a handheld manipulator configuration. As shown in FIG. 5A, after surgical access has been created, a first cutting tool is registered with the target tissue structure (228) and is operated to cut portions of the target tissue, at least partially removing the volume of bone within the desired cutting envelope (230). The first cutting tool may in one embodiment, for example, be coupled to a robotic arm, as described above in reference to FIG. 1D. A handheld manipulator and associated tool may then be utilized (232, 234), and automatic motion compensation conducted to mitigate relatively high frequency aberrant movement commands, such as those which may be associated with operator tremor (214).

Figure 5B:
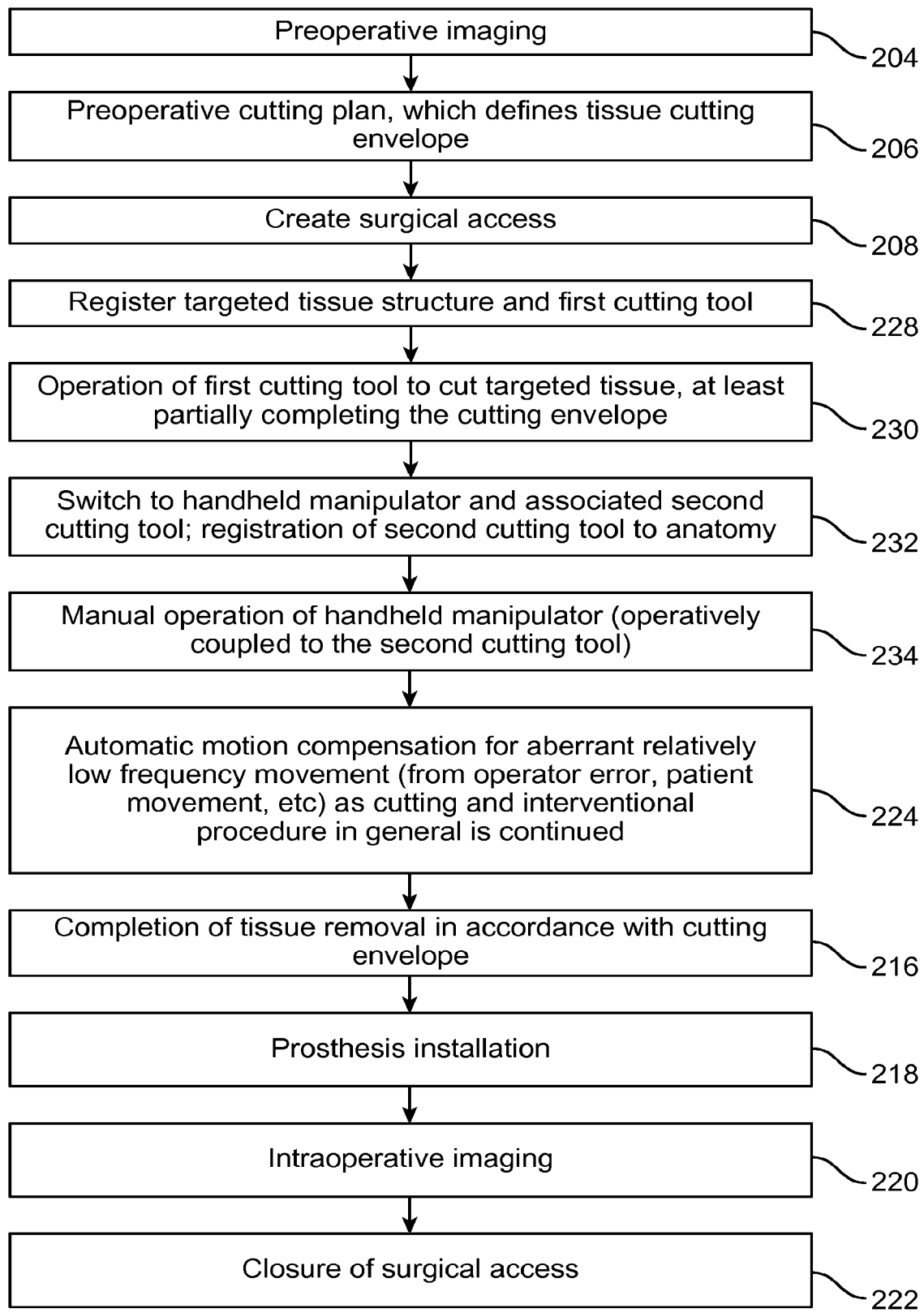

Referring to FIG. 5B, an embodiment similar to that of FIG. 5A is illustrated, with the exception that a controller is configured to conduct automatic motion compensation for aberrant commands of relatively low frequency (i.e., such as accidental commands that may result from operator error, patient movement, etc), while the cutting and interventional procedure in general is completed (224).

Figure 5C:
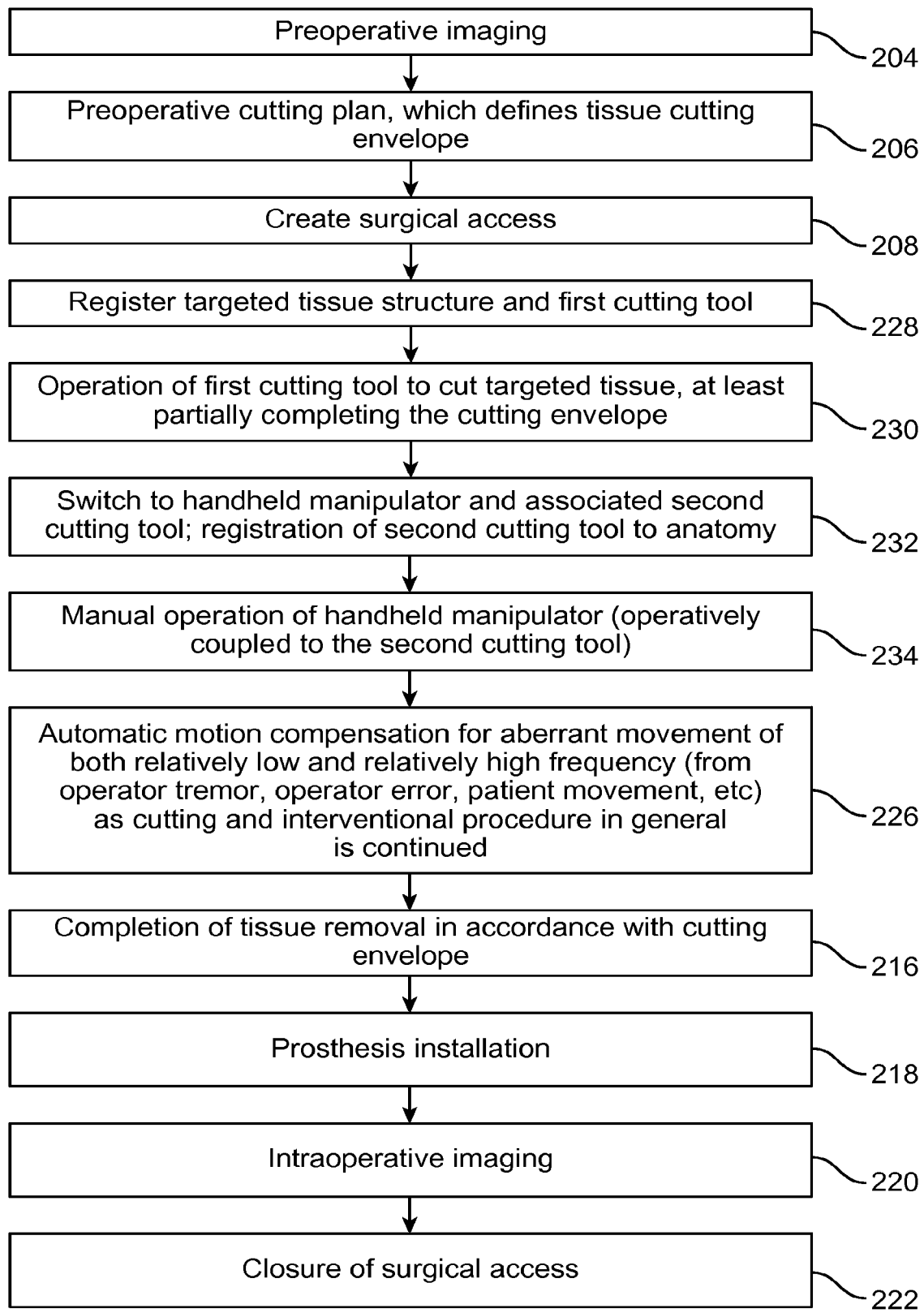

FIG. 5C illustrates an embodiment that combines the functionalities of the embodiments of FIGS. 5A and 5B, such that the controller is configured to conduct motion compensation for both relatively high, and relatively low frequency aberrant commands (226), to facilitate keeping the cutting tool within the desired bone cutting envelope.

In another embodiment, toolpath optimization in real or near-real time may be utilized to assist an operator in cutting out a targeted volume of tissue. For example, a tool path through the subject anatomy in the embodiments above may be controlled using automatic motion compensation, haptic resistance to particular tool positions (using, for example, an intercoupled haptic robotic arm system such as that discussed above 80 in reference to FIG. 1D), or both. And while tool path optimization is well known in certain applications such as CNC milling, wherein complete knowledge of the environment is coupled with complete control over the cutting tool, the scenario of a handheld surgical tool in the hands of a surgeon presents quite a different challenge given the fact that the surgeon is going to significantly contribute to the tool path with his manual control motions, and the fact that the control system generally has no prior knowledge of what the surgeon is going to do from a tool path perspective. In one embodiment, potential fields may be used to cause the tool to move autonomously toward small volumes marked as attractive (i.e., voxels of bone that has been targeted for removal, but which has not yet been in the bone cutting tool path), and away from small volumes marked as repulsive (i.e., voxels of bone that has been targeted for removal, and which has already been in the path of the bone cutting tool). Potential fields have been used, for example, to assist with controls paradigms for mobile robots avoiding obstacles on a floor, for example, as in Navigation of Mobile Robots Using Potential Fields and Computational Intelligence Means, Acta Polytechnica Hungarica Vol 4, No. 1, 2007, which is incorporated by reference herein in its entirety. In the subject embodiment, potential fields may be used to attract the tool path to uncut tissue that is to be cut under the surgical plan, and to repulse the tool path from tissue that has already been cut per the surgical plan, or from tissue that is not to be cut per the surgical plan—and again, the execution of such attraction or repulsion may be in the form of the control system actively attracting or repulsing the tool from a particular voxel or group thereof using haptic forces imparted to the handheld manipulator by a haptic subsystem, by the control system actively attracting or repulsing the tool from a particular voxel or group thereof using the automated motion compensation configurations described above, or by both haptics and motion compensation.

Figure 6A:
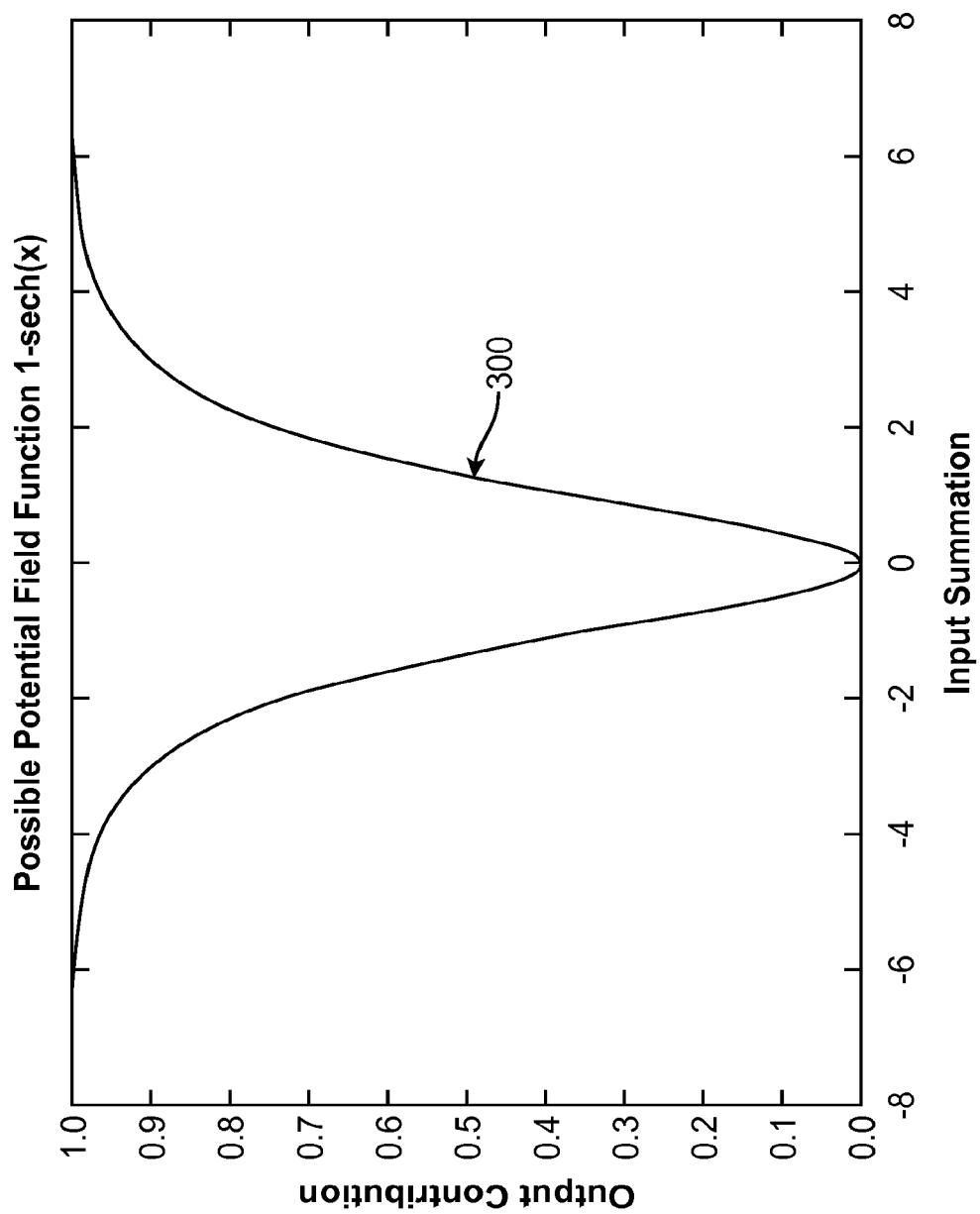

Referring to FIG. 6A, a sample potential field function is shown that is based upon a hyperbolic secant function (300) that can be used to attract or repulse the tool after the volume of tissue has been virtually divided into a three-dimensional mesh of voxels (302) with values assigned to each voxel in advance of the procedure based upon the surgical plan for cutting and removal, as shown in FIG. 6B. Referring to FIG. 6C, a bounding volume (304) such as a sphere for a substantially spherical bone cutting burr (with cutting tool centerpoint labeled as element 306), may be analyzed automatically in real or near-real time as intersecting with the voxel mesh (302); the values of the voxels in this effected intersecting volume may be numerically analyzed and summed in view of the potential field function (300), and the output from this summation may be used as an input in the controls scheme to alter the tool path—either attractively or repulsively. Further, the system may be configured to update the voxel values with updated tool path information; for example, when the tool goes through a voxel tagged as attractive per the surgical plan, it may then be tagged as repulsive since it has already encountered the tool, and the tool path optimization may continue to evolve, and to help the operator to remove all of the bone or other tissue, as per the preoperative plan. Further, the voxels representative of the edge of the predetermined cutting envelope may be always set to have a repulsive condition. In another embodiment, the tool path may be modulated automatically based upon a heuristic, such as a spatial state machine heuristic.

Figure 7:
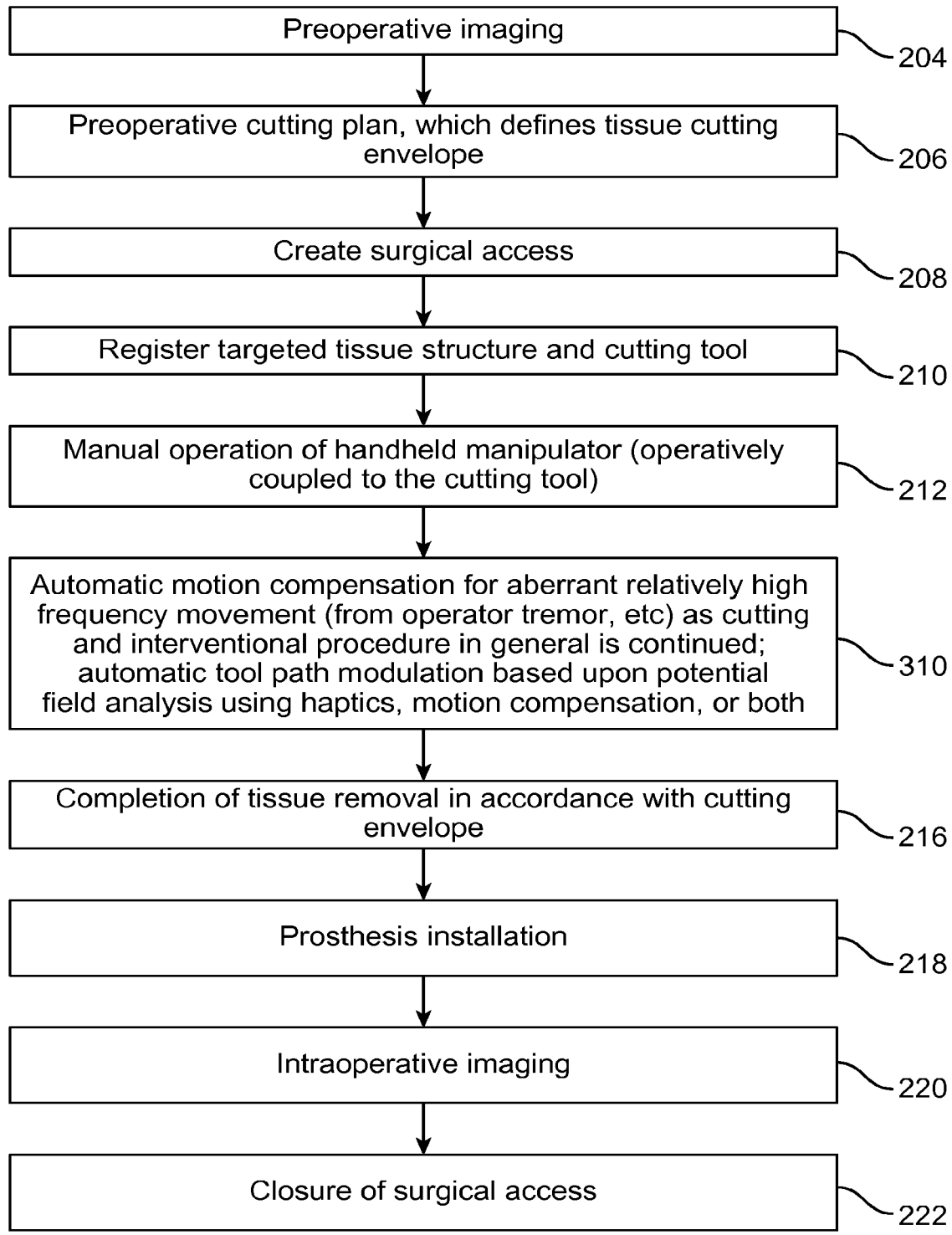
FIG. 7 illustrates aspects of an embodiment wherein potential fields may be utilized to further control motion of the interventional tool.

Referring to FIG. 7, an embodiment similar to that of FIG. 4A is illustrated, with the exception that with manual operation of the handheld manipulator (212) the control system is configured to not only execute automatic motion compensation to address aberrant relatively high frequency movement, but also to modulate the tool path automatically based upon potential field analysis, using haptics, motion compensation, or both. Similarly, potential field analysis may be added to any of the other abovedescribed configurations, such as those described in relation to FIGS. 4B-5C.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject interventions may be provided in packaged combination for use in executing such interventions. These supply "kits" further may include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) or polymer parts suitable for use as low friction bearing surfaces (such as ultra high molecular weight polyethylene) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity. The breadth of the present invention is not to be limited to the examples provided and/or the subject specification, but rather only by the scope of claim language associated with this disclosure.

What is claimed is:

1. A method for optimizing removal of a targeted volume of tissue defined by a tissue removal envelope, said method comprising the steps of:
    tracking a position of an end effector portion of a cutting tool relative to the targeted volume of tissue using a tracking subsystem;
    determining a tool path taken by the end effector portion relative to the targeted volume of tissue while a housing coupled to the cutting tool is manually grasped and manipulated by a user to remove a portion of the targeted volume of tissue with the end effector portion;
    marking a subvolume of the tissue removal envelope to represent the portion of the targeted volume of tissue removed with the end effector portion; and
    autonomously moving the end effector portion toward tissue that remains to be removed based on the marked subvolume of the tissue removal envelope so that the end effector portion avoids space in which tissue has already been removed thereby optimizing removal of the targeted volume of tissue.

2. The method of claim 1, wherein autonomously moving the end effector portion comprises moving the cutting tool with an actuator assembly controlled by a control system.

3. The method of claim 2, wherein moving the cutting tool comprises moving the cutting tool in two or more degrees of freedom.

4. The method of claim 2, wherein moving the cutting tool with the actuator assembly comprises operating a motor of the actuator assembly.

5. The method of claim 1, wherein tracking the position of the end effector portion of the cutting tool relative to the targeted volume of tissue comprises monitoring positions of one or more optical tracking markers that are associated with the end effector portion and the targeted volume of tissue.

6. The method of claim 1, further comprising acquiring image information for the targeted volume of tissue and analyzing the image information.

7. The method of claim 6, wherein acquiring the image information comprises acquiring the image information with a modality selected from the group consisting of: computed tomography, radiography, ultrasound, and magnetic resonance.

8. The method of claim 6, further comprising creating a preoperative surgical plan based at least in part upon the image information and utilizing the preoperative surgical plan to create the tissue removal envelope.

9. The method of claim 1, wherein marking the subvolume of the tissue removal envelope comprises tagging voxels of the tissue removal envelope as repulsive voxels.

10. The method of claim 9, further comprising tagging voxels of the tissue removal envelope as attractive voxels to represent the tissue that remains to be removed.

11. The method of claim 10, wherein autonomously moving the end effector portion toward the tissue that remains to be removed comprises moving the end effector portion based on the repulsive voxels and the attractive voxels.

12. The method of claim 1, further comprising representing the tissue removal envelope using voxels.

13. The method of claim 12, further comprising representing the end effector portion as a bounding volume.

14. The method of claim 13, wherein determining the tool path taken by the end effector portion comprises analyzing intersections of the bounding volume with the voxels representing the tissue removal envelope.

15. The method of claim 14, wherein marking the subvolume of the tissue removal envelope comprises updating tool path information for the intersected voxels to represent the portion of the targeted volume of tissue removed with the end effector portion.

16. A surgical system for optimizing removal of a targeted volume of tissue defined by a tissue removal envelope, the system comprising:
    a cutting tool comprising an end effector portion;
    a tracking subsystem for tracking a position of the end effector portion of the cutting tool relative to the targeted volume of tissue; and
    a controller operatively coupled to the bone cutting tool and configured to:
        mark a subvolume of the tissue removal envelope to represent the portion of the targeted volume of tissue removed with the end effector portion; and
        autonomously move the end effector portion toward tissue that remains to be removed based on the marked subvolume of the tissue removal envelope so that the end effector portion avoids space in which tissue has already been removed thereby optimizing removal of the targeted volume of tissue.

17. The system of claim 16, wherein the cutting tool is coupled to a handheld manipulator.

18. The system of claim 16, wherein the cutting tool is coupled to a robotic arm.

19. The system of claim 16, further comprising an actuator assembly for autonomously moving the end effector portion toward tissue that remains to be removed.

20. The system of claim 19, wherein the controller is further configured to tag voxels of the tissue removal envelope as attractive voxels to represent the tissue that remains to be removed.

* * * * *